(12) United States Patent
Yamaguchi

(10) Patent No.: US 10,012,665 B2
(45) Date of Patent: Jul. 3, 2018

(54) DISCHARGE DEVICE FOR LIQUID MATERIAL INCLUDING PARTICLE-LIKE BODIES

(75) Inventor: Shuichi Yamaguchi, Shiojiri (JP)

(73) Assignee: MICROJET CORPORATION, Shiojiri-shi, Nagano (JP)

( * ) Notice: Subject to any disclaimer, the term of this patent is extended or adjusted under 35 U.S.C. 154(b) by 190 days.

(21) Appl. No.: 13/577,826

(22) PCT Filed: Feb. 9, 2011

(86) PCT No.: PCT/JP2011/000736
§ 371 (c)(1),
(2), (4) Date: Oct. 25, 2012

(87) PCT Pub. No.: WO2011/099287
PCT Pub. Date: Aug. 18, 2011

(65) Prior Publication Data
US 2013/0037623 A1 Feb. 14, 2013

(30) Foreign Application Priority Data
Feb. 9, 2010 (JP) .................................. 2010-026654

(51) Int. Cl.
*B05B 1/00* (2006.01)
*G01N 35/10* (2006.01)
*B01L 3/02* (2006.01)

(52) U.S. Cl.
CPC ........ *G01N 35/1016* (2013.01); *B01L 3/0268* (2013.01); *B01L 2200/061* (2013.01);
(Continued)

(58) Field of Classification Search
CPC .... B05C 11/1034; B05C 5/0216; B41J 2/195; B41J 2/04581; B41J 2/09; B41J 2/125;
(Continued)

(56) References Cited

U.S. PATENT DOCUMENTS 4,325,483 A * 4/1982 Lombardo et al. ............ 209/3.1
4,928,125 A * 5/1990 Iino ................................ 347/54
(Continued)

FOREIGN PATENT DOCUMENTS

JP 2000-180347 A1 6/2000
JP 2005-090986 A 4/2005
(Continued)

OTHER PUBLICATIONS

Notification of Transmittal of Translation of the International Preliminary Report on Patentability (Chapter I or Chapter II)(PCT/IB/338) and International Preliminary Report on Patentability (Translation)(Form PCT/IB/373) dated Oct. 11, 2012, in corresponding International Application No. PCT/JP2011/000736. (6 pages).

(Continued)

*Primary Examiner* — Luke D Ratcliffe
*Assistant Examiner* — Vicente Rodriguez
(74) *Attorney, Agent, or Firm* — Buchanan Ingersoll & Rooney PC

(57) ABSTRACT

A discharge device includes a discharge head that discharges a liquid material from a nozzle opening connected to the cavity by varying the internal pressure of a cavity using an actuator. The discharge head includes a monitoring portion provided between the cavity and the nozzle opening and the discharge device further includes a detection apparatus that detects the number and/or form of the particle-like bodies included in the liquid material in the monitoring portion of the discharge head and a control unit that drives the actuator according to the detection result of the detection unit to change the state of the particle-like bodies included in the liquid material of the monitoring portion.

28 Claims, 14 Drawing Sheets

(52) U.S. Cl.
CPC .................. *B01L 2200/0647* (2013.01); *B01L 2200/0657* (2013.01); *G01N 2035/1041* (2013.01)

(58) Field of Classification Search
CPC ... B41J 2002/022; B41J 29/393; B07C 5/342; B07C 5/3425; B07C 5/3416; B07C 5/04; G01N 15/1484; B01L 2300/0819; B01L 2300/0861; B01L 2300/0864; B01L 2300/0877; B01L 2300/14; B01L 3/502761
USPC ........................ 356/4.03; 347/6, 74
See application file for complete search history.

(56) References Cited

U.S. PATENT DOCUMENTS

| | | | | |
|---|---|---|---|---|
| 5,721,433 | A | * | 2/1998 | Kosaka .................. 250/573 |
| 6,019,455 | A | * | 2/2000 | Taylor et al. ............. 347/54 |
| 6,281,018 | B1 | * | 8/2001 | Kirouac ............... G01N 15/14 356/73 |
| 6,367,925 | B1 | * | 4/2002 | Chen et al. .............. 347/109 |
| 6,522,781 | B1 | | 2/2003 | Norikane et al. |
| 7,392,908 | B2 | * | 7/2008 | Frazier ............... G01N 15/1459 209/3.1 |
| 7,428,047 | B2 | * | 9/2008 | Oldham ............... B82Y 10/00 356/344 |
| 2006/0285430 | A1 | | 12/2006 | Seto |
| 2008/0096285 | A1 | | 4/2008 | Koyata et al. |
| 2008/0257072 | A1 | | 10/2008 | Takahashi et al. |
| 2012/0078531 | A1 | * | 3/2012 | Lo ...................... G01N 15/1459 702/21 |

FOREIGN PATENT DOCUMENTS

| | | |
|---|---|---|
| JP | 2005-238787 A | 9/2005 |
| JP | 2006-349638 A | 12/2006 |
| WO | WO 2005/103642 A1 | 11/2005 |
| WO | WO 2006/011531 A1 | 2/2006 |

OTHER PUBLICATIONS

International Preliminary Examination Report (Chapter 2) (Form PCT/IPEA/409) dated Jan. 10, 2012, issued in corresponding International Application No. PCT/JP2011/000736. (12 pages).

International Search Report (PCT/ISA/210) dated Apr. 12, 2011, by the Japanese Patent Office as the International Searching Authority for International Application No. PCT/JP2011/00736.

* cited by examiner

DISCHARGE DEVICE FOR LIQUID MATERIAL INCLUDING PARTICLE-LIKE BODIES

TECHNICAL FIELD

The present invention relates to a device and method for discharging liquid material including particle-like bodies.

BACKGROUND ART

Japanese Laid-Open Patent Publication No. 2005-238787 (hereinafter "Document 1") discloses an ink discharge amount measuring method for measuring the discharge amount of an ink droplet discharged from a nozzle of an ink jet head. This method finds the ink discharge amount by carrying out a step of discharging an ink droplet from a nozzle onto an ink droplet shape evaluating jig, a step of measuring the diameter of the ink droplet discharged onto the ink droplet shape evaluating jig, and a step of calculating the ink discharge amount from the diameter of the measured ink droplet based on correlation found in advance between the diameter of an ink droplet and the ink discharge amount.

DISCLOSURE OF THE INVENTION

The use of ink jet technology developed for printer apparatuses to discharge ink and other substances onto printing paper or other materials is being investigated. As the material to be discharged, research is being conducted not only into simple liquid materials (which includes liquids and materials that exhibit fluidity such as solutions) but also liquid materials (mixtures) including particle-like bodies (particles, fine particles, particulate material, granulated substrate) which includes for example living materials (organisms) like cells and genes, and solids like metals, oxides, or the like. In applications that discharge particle-like bodies such as cells, it is necessary to discharge precisely according to predetermined conditions from the nozzle of an ink jet head toward a target such as a microplate.

One aspect of the present invention is a discharge device including a discharge head that discharges a liquid material from a nozzle opening connected (fluidly connected) to the cavity by varying the internal pressure of the cavity using an actuator. The discharge head includes a monitoring portion (detection portion) provided between the cavity and the nozzle opening. The discharge device further includes a detection apparatus that detects the number and/or form of particle-like bodies included in the liquid material in the monitoring portion of the discharge head and a control apparatus that drives the actuator according to the detection result of the detection unit to change a state of the particle-like bodies included in the liquid material of the monitoring portion.

With this discharge device, it is possible, via the monitoring portion (detection portion), to acquire a detection result including the number and/or form of the particle-like bodies (for example, cells) included in the liquid material to be discharged next timing. This means that with this discharge device, it is possible to confirm the state of the liquid material, especially the state of the particle-like bodies included in the liquid, immediately before discharge.

In addition, this discharge device is capable of varying the internal pressure of the cavity by driving an actuator and therefore able to change the state of the particle-like bodies included in the liquid material in the monitoring portion fluidly connected to the cavity. Accordingly, the control apparatus is capable of changing the state of the particle-like bodies included in the liquid material in the monitoring portion any number of times until the detection result is within a range of a predetermined condition for discharging. For this reason, the discharge device is capable of precisely controlling the number and/or form of the particle-like bodies included in the liquid material discharged onto a target.

A typical method (means) of changing the state of the particle-like bodies included in the liquid material in the monitoring portion is to discharge the liquid material. Accordingly, the control apparatus should preferably include a function (discharge target selection function unit) that changes the discharge target of the liquid material according to the detection result. If the discharge device discharges onto a plurality of targets with different discharge conditions, by discharging the liquid material onto a target for which the detection result (detected condition of the particle-like bodies included in the liquid material) matches, it is possible to change the state of the particle-like bodies included in the liquid material in the monitoring portion. Also, by changing the discharge target of the liquid material and disposing of the liquid material at a different location to the target(s), it is possible to change the state of the particle-like bodies included in the liquid material in the monitoring portion.

It is also possible to change the state of the particle-like bodies included in the liquid material in the monitoring portion by driving an actuator to agitate the liquid material in the monitoring portion without having the liquid material discharged from the nozzle opening. It is effective for the control apparatus to include a function (agitation function unit) that agitates the liquid material in the monitoring portion according to the detection result without having the liquid material discharged from the nozzle opening. By doing so, it is possible to suppress consumption of the liquid material and the particle-like bodies.

In this discharge device, the monitoring portion of the discharge head should preferably include an oblate flattened portion where a cross section of a flow path from the cavity to the nozzle opening of the discharge head extends like oblate in a first direction, the flattened portion dispersing the particle-like bodies in the first direction. The nozzle opening of the discharge head may be shaped or molded by being flattened so as to extend in the first direction.

Since the monitoring portion internally includes a flattened space, the particle-like bodies included in the liquid material are dispersed in the first direction and it becomes easier to determine the number and form (such as the size (diameter), shape, and color) of the particle-like bodies and thereby obtain the detection result more clearly. For this reason, in the discharge device, even when the particle-like bodies included in the liquid material are particle-like bodies with a comparatively small particle diameter, it is easy to precisely confirm the form (type) of the particle-like bodies included in the liquid material before discharge. Accordingly, the discharge device is capable of discharging particle-like bodies toward targets according to predetermined conditions with much higher precision and reliability.

With this discharge device, it is preferable for the monitoring portion of the discharge head to be light transmissive (transparent) and for the discharge device to include an image pickup unit that carries out image recognition on a plurality of the particle-like bodies using light. With this discharge device, it is possible to observe the particle-like bodies included in the liquid material using visible light. The image pickup unit is typically a camera equipped with an image pickup element such as a CCD or a CMOS and an optical lens, and by having a processor carry out image processing on an image obtained by the image pickup unit, it is easy to distinguish even minute particles such as cells. In particular, by using an image pickup apparatus with a parallel processing feature as the image pickup unit, it is possible to detect minute particles present in the monitoring portion at high speed. Also, since it is possible to include a fluorescent-colored material in a living material such as cells, in such case it is possible to illuminate the material with light aside from visible light that can detect fluorescence, such as "black light", and observe the material using a camera capable of detection.

In this discharge device, the monitoring portion should preferably include a first region that is connected or next to the nozzle opening and a second region that follows the first region, and the detection apparatus should preferably acquire the number and/or form in the first region and the number and/or form in the second region of the monitoring portion. The control apparatus should preferably be operable, when the detection result of the first region is outside a range of a predetermined condition or when the detection result of the second region is outside a range of a predetermined condition, to change the state of the particle-like bodies included in the liquid material in the monitoring portion. The discharge device discharges the liquid material onto a target only when the detection result of the first region and the detection result of the second region are in the ranges of predetermined conditions. This means that it is possible to further improve the precision of the number and/or form of the particle-like bodies injected into the target.

In the discharge device, the actuator should preferably be a piezo element, and the control apparatus should preferably include a feature or functional unit that supplies drive pulses of a pushing type (pushing method) to the piezo element when the liquid material is to be discharged.

Another aspect of the present invention is a discharge head that discharges a liquid material from a nozzle opening connected to the cavity by varying the internal pressure of a cavity using an actuator. The discharge head includes a monitoring portion provided between the cavity and the nozzle opening. The monitoring portion disperses a plurality of particle-like bodies included in the liquid material to be discharged from the nozzle opening. The monitoring portion of the discharge head should preferably include an oblate flattened portion where a cross section of a flow path from the cavity of the discharge head to the nozzle opening extends in a first direction, the flattened portion dispersing the plurality of particle-like bodies in the first direction. The nozzle opening of the discharge head should preferably be shaped (molded) so as to be flattened so as to extend in the first direction.

In this discharge head, it is preferable for the monitoring portion to be light transmissive. The monitoring portion of the head typically includes a first side wall and a second side wall that are flat and are disposed facing one another. Since the cross section of the flow path in the monitoring portion is rectangular or a similar shape, across the entire monitoring portion, it is difficult for the plurality of particle-like bodies to become placed on top of one another (overlapped on each other) in the narrowed direction between the first side wall and the second side wall, which improves the probability that the individual particles can be individually detected.

The discharge head should preferably include a tubular member that holds the liquid material and part of which is shaped or molded so as to form the cavity whose internal pressure is varied by an actuator attached to an outside, the nozzle opening being provided at one end of the tubular member, and the monitoring portion should preferably be provided between the cavity of the tubular member and the nozzle opening. Since it is possible to seamlessly form the parts from the cavity to the nozzle opening via the monitoring portion from one tubular member, for example, a glass tube, it is possible to provide a discharge head that less shows stagnation and blockages due to bubbles and the like and is suited to discharging a wide variety of particle-like bodies and liquid materials.

The monitoring portion can be formed by squeezing a part of the tubular member from the outside. A typical example of the tubular member is one of a glass tube, a resin tube, and a ceramic tube that is translucent.

Yet another aspect of the present invention is a method of discharging a liquid material including particle-like bodies onto a target using a discharge device. The discharge device includes a discharge head that varies the internal pressure of a cavity using an actuator to discharge the liquid material from a nozzle opening connected to the cavity, a control apparatus that controls the actuator, and a detection apparatus that detects the particle-like bodies included in the liquid material in the monitoring portion provided between the cavity and the nozzle opening. The method includes the following steps.

1. The control apparatus acquiring, from the detection apparatus, a detection result including a number and/or form of the particle-like bodies included in the liquid material.
2. Changing a state of the particle-like bodies included in the liquid material in the monitoring portion by driving the actuator according to the detection result.

The changing a state (step 2) includes agitating the liquid material in the monitoring portion without having the liquid material discharged from the nozzle opening according to the detection result. The changing a state may include changing a discharge target of the liquid material according to the detection result. The changing the discharge target may include disposing of the liquid material.

The acquiring the detection result (step 1) should preferably include setting, in the monitoring portion, a first region that is connected to the nozzle opening and a second region that follows the first region, and acquiring the detection result for the first region and the detection result for the second region. Also, The changing a state (step 2) should preferably include changing the state of the particle-like bodies included in the liquid material in the monitoring portion when the detection result of the first region is outside a range of a predetermined condition or when the detection result of the second region is outside a range of a predetermined condition.

DETAIL DESCRIPTION

Figure 1:
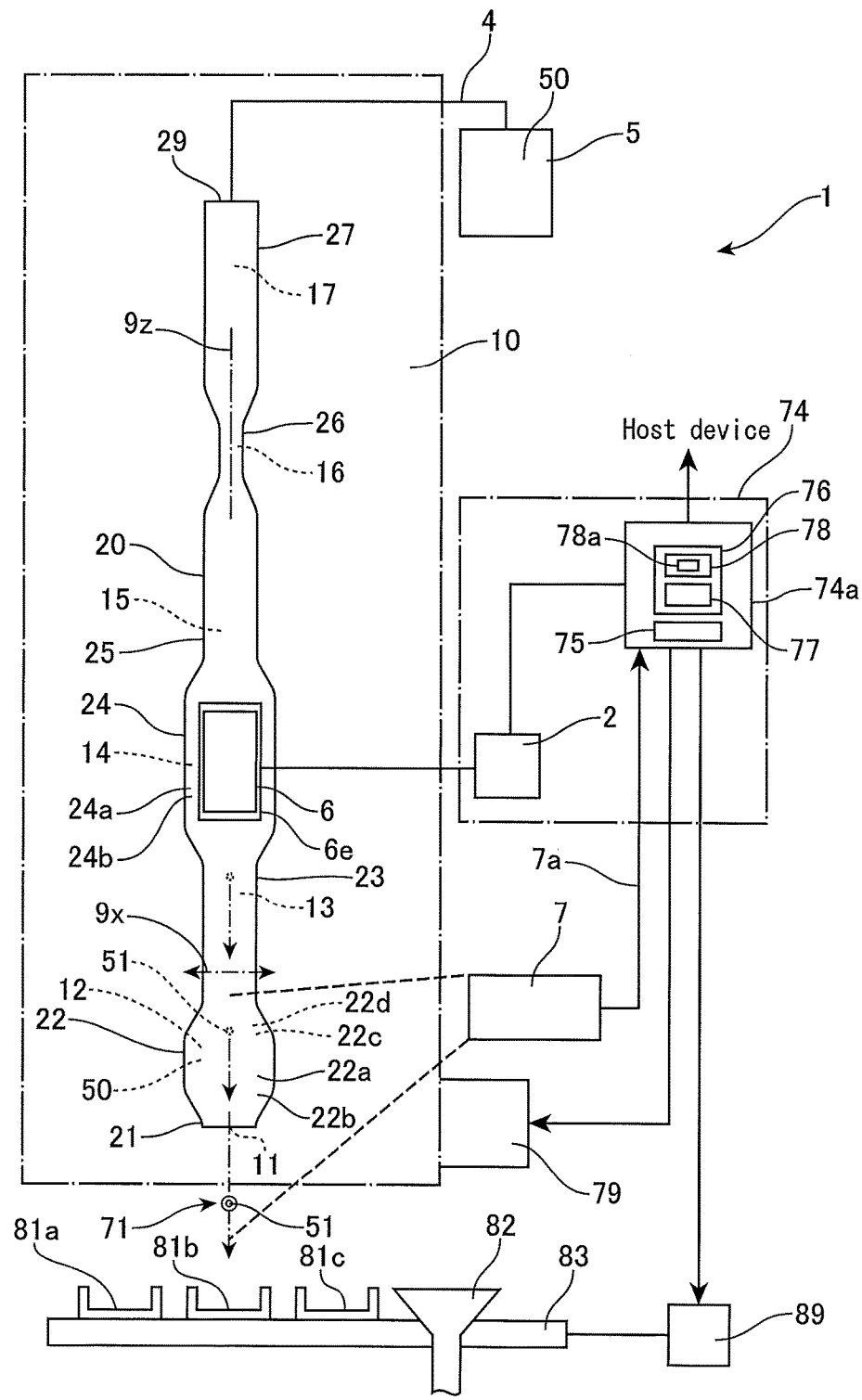
FIG. 1 shows an outline of a discharge device according to the present invention.

FIG. 1 shows the outline of a discharge device according to a first embodiment of the present invention. The discharge device 1 includes a discharge head (nozzle head, or nozzle head driven according to an ink jet method) 10 equipped with a glass tube 20 that is a tubular member, a vessel or container 5 storing a liquid material 50 discharged from the discharge head 10 for example, a carrier such as water, a first actuator 6 for discharging a droplet 71 from the discharge head 10, a driving unit (apparatus) 2 that drives the first actuator 6, a detection unit (apparatus) 7 that detects the state of the droplet 71 immediately before and immediately after discharge from the discharge head 10, a second actuator 79 that moves or travels the discharge head 10, a table 83 that supports a plurality of targets 81a, 81b, and 81c on which the discharge head 10 discharges a droplet or droplets 71, a third actuator 89 that moves or travels the table 83, and a control unit (apparatus) 74 that controls the movement actuators 79 and 89.

A disposer 82 for disposing of a droplet 71 from the discharge head 10 is provided on the table 83. In the discharge device 1, by moving the table 83 using the third actuator 89 or moving the discharge head 10 using the second actuator 79, it is possible for the droplet 71 from the discharge head 10 to be injected into one of the targets 81a to 81c or to be disposed of by the disposer 82. The targets 81a to 81c only need to receive the droplet 71 and as examples may be petri dishes, analysis plates, test tubes, or the like.

The discharge head 10 includes the glass tube (tubular member) 20 that extends in substantially a straight line. On the glass tube 20, a front end part 21 is a nozzle opening 11 that is flattened (i.e., has a flat shape), a part (first flattened portion) 22 that is joined (connected, fluidly connected) to the front end part 21 and extends back from the front end part 21 is a flattened monitoring portion (detection portion) 12 that includes the nozzle opening 11, and a part (second flattened portion) 24 that is joined (connected, fluidly connected) to the first flattened portion 22 and extends back from the first flattened (flat) portion 22 is a flattened cavity (pressure chamber) 14. Also, the end (rear end) 29 of the glass tube 20 is connected via a supply tube 4 to the vessel 5.

The entire tubular member 20 that includes the flattened parts 21, 22, and 24 is light transmissive (transparent, translucent) and is shaped (formed or molded) from a single glass tube according to an appropriate method (using a mold, for example). Accordingly, a seamless flow path is formed from the cavity 14 via the monitoring portion 12 to the nozzle opening 11 inside the glass tube 20 of the discharge head 10.

The discharge head 10 includes a plate-like piezoelectric element (piezo element, actuator) 6 attached to a surface (outer surface) on an outside of a flat wall 24a of the cavity 14 of the glass tube 20. The control unit 74 includes a driving unit 2 that drives the piezoelectric element 6 to change the internal pressure of the cavity 14 and discharge a liquid material 50 from the nozzle opening 11 connected to the cavity 14 as the droplet 71. The control unit 74 is also capable of driving the piezoelectric element 6 to produce an amount of pressure that agitates the liquid material 50 inside the glass tube 20 including the monitoring portion 12 but does not cause the liquid material 50 to be discharged from the nozzle opening 11.

Between the cavity 14 and the nozzle opening 11, the glass tube 20 of the discharge head 10 includes the flattened monitoring portion (detection portion, observation chamber, detection chamber) 12 where the cross section of the flow path extends in a direction (first direction) 9x which is perpendicular to a center axis 9z of the glass tube 20. In the flattened monitoring portion 12 that includes such flattened internal cross-section, a plurality of particle-like bodies (particles) 51 included in the liquid material 50 to be discharged from the nozzle opening 11 are dispersed in the first direction 9x. The monitoring portion 12 has a flattened cross-section and side walls 22a and 22c are substantially flat that facilitates observation of the inside of the monitoring portion 12 with image picking up images of an inside of the monitoring portion 12 since refraction and total internal reflection of light are suppressed. Also, flattened monitoring portion 12 does not have or has little part where the inside thereof cannot be seen. This means that the particle-like bodies 51 included in the liquid material 50 can be precisely observed via the transparent and flat side walls 22a and 23c of the monitoring portion 12.

The monitoring portion 12 holds the liquid material 50 to be discharged next timing (immediately before discharge) from the nozzle opening 11, and if a plurality of the particle-like bodies 51 are included in the liquid material 50 immediately before discharge, it is possible to disperse such bodies in the direction 9x perpendicular to the flow and to independently detect (observe) the plurality of particle-like bodies 51 with a high probability. Accordingly, with this discharge device 1, if, in the monitoring portion 12, particle-like bodies 51 are included in the liquid material 50 immediately before discharge, it will be possible to acquire information on not only the number of such bodies 51 but also the properties (form or state) of the particle-like bodies 51, such as the diameter (size), shape, pattern, and color. This means that the detection unit 7 is capable of specifying the type (kind) of particle-like bodies 51 included in the liquid material 50 in the monitoring portion 12. Accordingly, the detection unit 7 can output a detection result 7a including the number and/or form of the particle-like bodies 51 included in the liquid material 50 of the monitoring portion 12.

By driving the piezo element 6 based on the detection result (measurement result) 7a of the monitoring portion 12 to apply vibration that agitates the liquid material 50 in a range where the liquid material 50 is not discharged or that discharges the liquid material 50 onto one of the targets 81a to 81c or the disposer 82, in the discharge device 1, the internal state of the monitoring portion 12 can be changed to the state where the bodies 51 are appropriately disposed. That enables liquid material 50 including only an indicated or predetermined number and/or form (i.e., particle-like bodies of the predetermined type judged from the form) of the body 51 or the bodies 51 to be discharged onto one of the predetermined targets 81a to 81c.

In the discharge device 1, an instruction (or "signal") in the control unit 74 is received by the driving unit (or "driving apparatus" or "driver") 2, and the driver 2 drives the actuator 6 using drive pulses. The control unit 74 may be an apparatus equipped with hardware resources of a general purpose computer such as a CPU and a memory, or may be a control unit equipped with hardware, including an LSI, an ASIC, or the like, that is dedicated to the discharge device 1. It is desirable for the control unit 74 to include a function for communicating with a host apparatus such as a personal computer. Also, the control unit 74 may be installed in a personal computer that serves as a host apparatus, or functions as the control unit 74 may be provided by appropriate software (or "program" or "program product").

When the piezo element 6 that is the actuator expands or contracts and/or deforms due to the drive pulses, the flat wall 24a of the cavity 14 provided in the glass tube 20 becomes displaced, producing fluctuations in the internal volume of the cavity 14. For this reason, the internal pressure of the cavity 14 changes and the liquid material 50 supplied from the vessel 5 is supplied to the monitoring portion 12 via the cavity 14. By the internal pressure changes in the cavity 14, the liquid material 50 held in the monitoring portion 12 is also pushed out from the nozzle opening 11 provided at the front end part 21 of the glass tube 20 and is discharged as a droplet 71. When doing so, if any particle-like bodies 51 are mixed into the liquid material 50 held in the monitoring portion 12, liquid material 50 including such particle-like bodies 51 is discharged from the nozzle opening 11.

The control unit 74 includes a head controller 74a, and the head controller 74a includes a function (acquisition unit) 75 acquiring the detection result 7a of the detection unit 7 and a function (state changing unit) 76 that changes the state of the particle-like bodies 51 included in the liquid material 50 of the monitoring portion 12 according to the detection result 7a. The state changing unit 76 includes a discharge target changing function (discharge target changing unit) 78 that controls the piezo element 6 and the actuators 79 and/or 89 so as to discharge the liquid material 50 onto a predetermined one of the targets 81a to 81c if, according to the detection result 7a of the detection unit 7, the number and/or form or the like of the particle-like bodies 51 included in the liquid material 50 immediately before discharge satisfies a predetermined condition. The discharge target changing unit 78 includes a disposal function (disposal unit) 78a that controls the piezo element 6 and the actuators 79 and/or 89 so as to dispose the liquid material 50 into the disposer 82 and change the state of the monitoring portion 12. The state changing unit 76 also includes a function (agitating unit) 77 that drives the piezo element 6 to an extent where the liquid material 50 is not discharged but change the state of the particle-like bodies 51 in the liquid material 50 of the monitoring portion 12 if, according to the detection result 7a of the detection unit 7, the number and/or state of the particle-like bodies 51 included in the liquid material 50 immediately before discharge does not satisfy the predetermined condition.

In this way, the discharge device 1 is capable of discharging or dispensing the liquid material 50 including various particle-like bodies 51 on the target 81 using the an ink-jet type discharge head 10, with detecting or confirming the number and form (external appearance, state) of the particle-like bodies 51 included in the liquid material 50 immediately before discharge inside the discharge head 10. In this specification, the particle-like bodies 51 may be any material that is independently present in the liquid material 50 and whose presence may be detected (identified or recognized) using various methods via the glass tube 20. A typical detection method includes image processing using light (visible light, infrared light, or the like), with it being effective to acquire an image that has been enlarged by an appropriate lens system. The detection method may be a method that uses a magnetic field or an electric field. Particle-like bodies (particles, fine particles) 51 including biological materials such as cells and genes (DNA, RNA) can be given as examples of typical particle-like bodies 51. The particle-like bodies 51 include not only spherical matter (grains) but also matter that is linear or other shapes.

Such particle-like bodies 51 will often become blocked or unevenly distributed in the range from the cavity 14 to the nozzle opening 11. From the cavity 14 to the nozzle opening 11 including the monitoring portion 12 those are the main parts of the discharge head 10 of the discharge device 1 are seamlessly formed by a single glass tube 20. This means that the discharge head 10 is resistant to or does not show stagnation, blockages, and uneven distribution due to air bubbles or the like, and in the discharge head 10, even particle-like bodies 51 that are susceptible to blockages, such as cells, can be guided to the nozzle opening 11 in a state where the particle-like bodies 51 are comparatively uniformly present in the liquid material 50.

Figure 2:
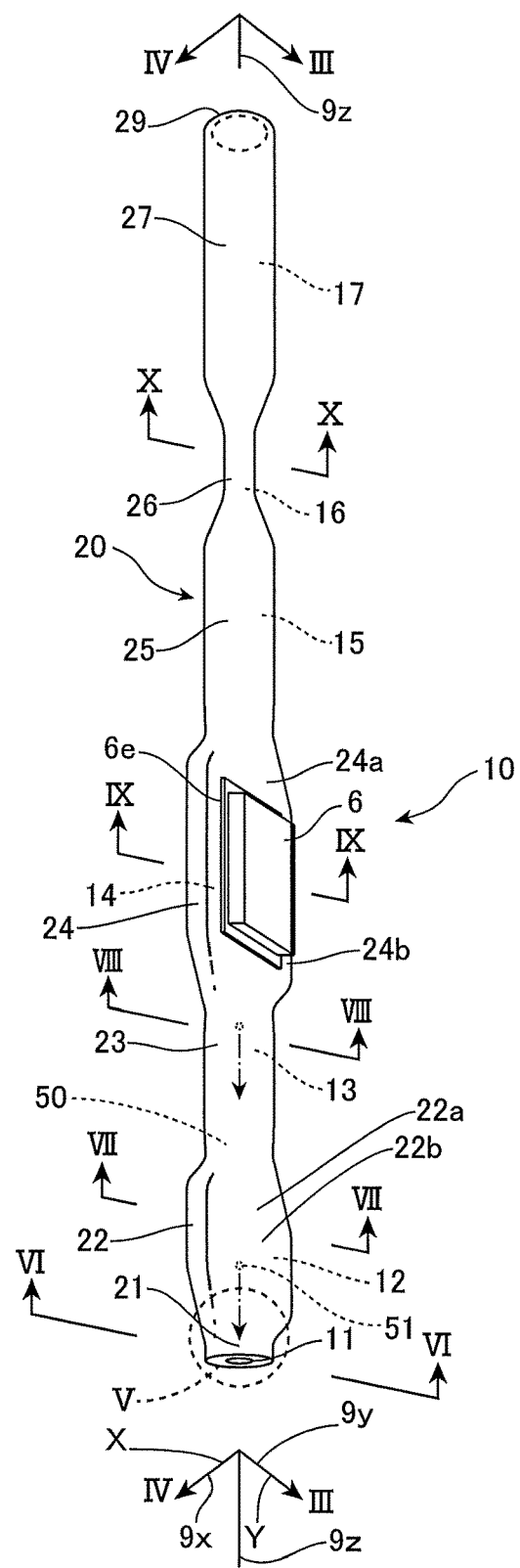
FIG. 2 is a perspective view showing an enlargement of the construction of a discharge head.
Figure 3:
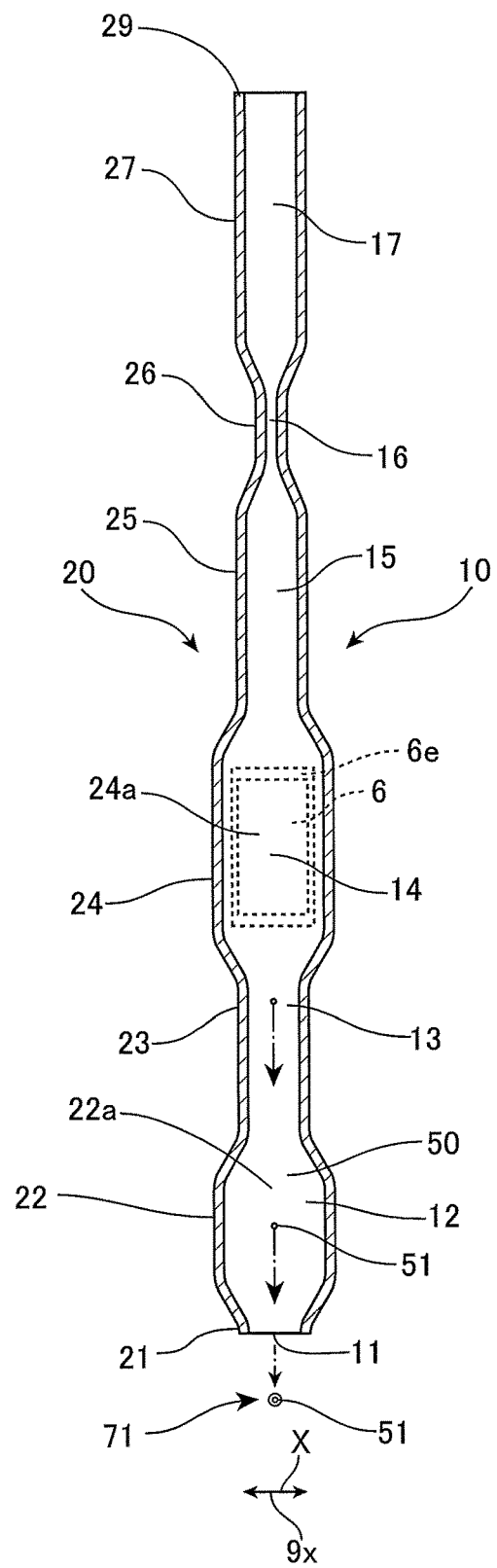
FIG. 3 is a cross-sectional view showing a cross section in the length direction of the discharge head.
Figure 4:
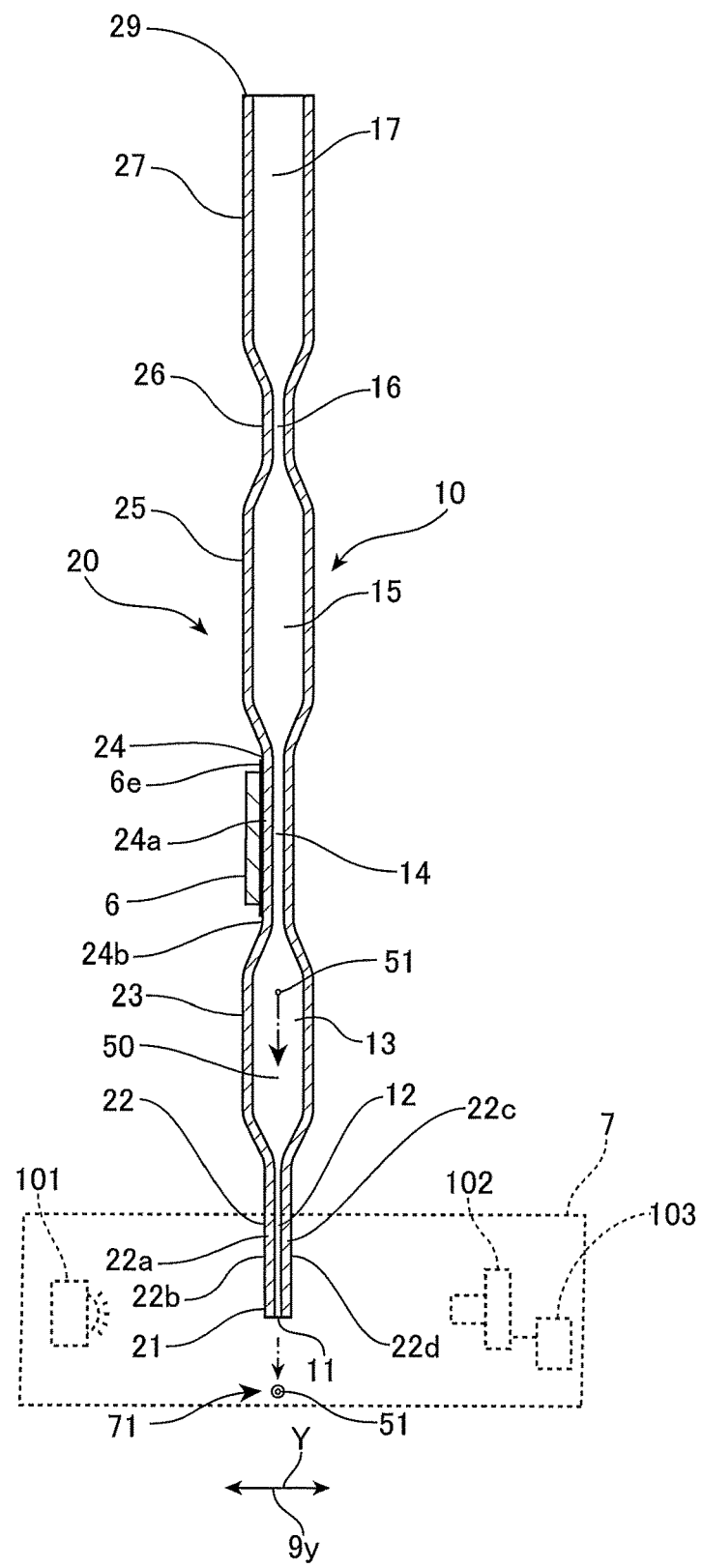
FIG. 4 is a cross-sectional view showing a different cross section in the length direction of the discharge head.

FIG. 2 shows an enlargement of the construction (arrangement) of the glass tube 20 of the discharge head 10. FIGS. 3 and 4 show the overall construction of the glass tube 20 by way of cross sections that include the first direction 9x (hereinafter, X direction) that is perpendicular to the length direction (center axis) 9z and the second direction 9y (hereinafter, Y direction) that is perpendicular to the center axis 9z and the first direction 9x. A typical size of the glass tube 20 is an external diameter of 0.5 to 5 mm and a thickness of 0.01 to 1 mm. The glass tube 20 includes the front end part 21 that is toward the nozzle opening 11 at the front end and formed (molded) in a flat shape that is wide in the X direction and narrow in the Y direction, the first flattened portion 22 that is to the rear of (above in FIG. 2) the front end part 21 and is formed (molded) in a flat shape that is wide in the X direction and narrow in the Y direction, a first cylindrical portion 23 that is to the rear of the first flattened portion 22 and is substantially cylindrical, the second flattened portion 24 that is to the rear of the first cylindrical portion 23 and is formed (molded) in a flat shape that is wide in the X direction and narrow in the Y direction, a second cylindrical portion 25 that is to the rear of the second flattened portion 24 and is substantially cylindrical, a narrowed portion 26 that is to the rear of the second cylindrical portion 25 and is narrower than the second cylindrical portion 25, and a third cylindrical portion 27 that is to the rear of the narrowed portion 26, is substantially cylindrical, and is used to connect the glass tube 20 to the supply tube 4. The front end part 21, the first flattened portion 22, and the second flattened portion 24 may be flattened in different directions. For example, the second flattened portion 24 may be molded in a flat shape so as to be wide in the Y direction and narrow in the X direction.

The various parts are described in more detail. First, as shown by the enlargement in FIG. 5, the front end part 21 of the glass tube 20 is formed (molded) by squeezing the front end of the glass tube 20 from the outside into an appropriate size for the nozzle opening 11. A cross section of the front end part 21 is shown in enlargement in FIG. 6. Since the nozzle opening 11 is molded into a flat shape that is wide in the X direction and narrow in the Y direction and whose cross-sectional form is flattened into substantially an oblate (oval) or a similar shape, it becomes easy for the particle-like bodies 51 to become uniformly dispersed in the X direction and to visually confirm or detect the particle-like bodies 51 immediately before discharge. A typical size of the nozzle opening 11 internally has a maximum height (maximum inner diameter) d in the Y direction of 15 to 200 µm. To discharge minute particle-like bodies 51 such as cells of the order of µm, the amount of the liquid material 50 discharged from the nozzle opening 11 in a single operation should preferably be controlled to a range from pl (picoliter) order to fl (femtoliter) order. Although one method of forming the front end part 21 is to heat the glass tube 20 and then press the glass tube 20 from the up-down direction (a direction perpendicular to the length direction), it is possible to use a variety of known glass working methods and the method of working is not limited to this example.

Note that the expression "oblate (oval)" in the present specification refers to an elongated circle which excludes shapes with corners, such as a rectangle or a square, and also excludes a perfect circle. The oblate (oval) includes, in addition to an oval, a concept that includes a variety of shapes such as shapes where a rectangle or square with semicircles arranged at opposing sides with a diameter equal to the distance between the opposing sides (or "gap between opposing sides").

Figure 7:
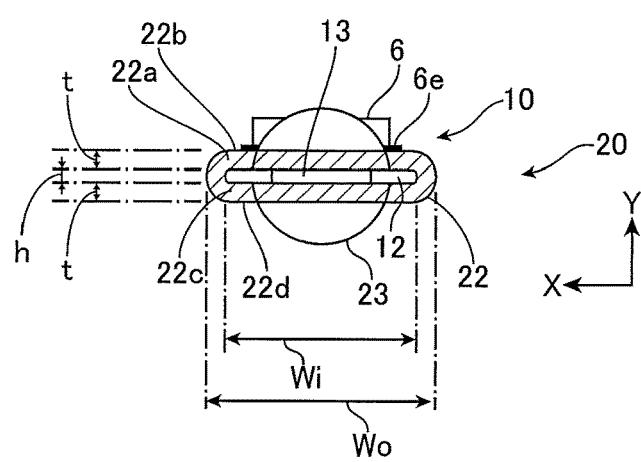
FIG. 7 is a cross-sectional view showing a flattened part of the discharge head.

The first flattened portion 22 to the rear or back of (next to) the front end part 21 is formed by squeezing the glass tube 20 from outside and is a part that constructs the monitoring portion 12 with a flattened or box-like space formed inside. FIG. 7 shows an enlargement of the cross section. A typical size of the first flattened portion 22 internally has the maximum height (maximum diameter) h in the Y direction of 0.05 to 1.0 mm, a maximum width Wi in the X direction of around 0.3 to 10 mm, and an internal length in the length direction 9z of 1 to 20 mm. The maximum internal width Wi should more preferably be around 1 to 3 mm. The first side wall 22a and the second side wall 22c are plate-like and extend in the X direction so that the particle-like bodies present in the monitoring portion 12 can be observed through the walls, the wall thickness t should preferably be around 50 to 500 µm or more preferably around 50 to 300 µm. The first flattened portion 22 is formed so that the external maximum width Wo is around 0.55 to 7 mm.

In the present embodiment, the first flattened portion 22 is molded or formed by squeezing the glass tube 20 from outside and has the monitoring portion 12 with a flattened opening that is substantially oblate (oval) or a similar shape formed inside. The volume of the monitoring portion 12 is set by the internal cross-sectional area and the length, and is important in view of the method in which the monitoring portion 12 is used. That is because the detection algorithm for the particle-like bodies 51 described below will change according to how many discharge amounts are held in the monitoring portion 12.

The maximum height (maximum internal diameter) h in the Y direction of the monitoring portion 12 should preferably be selected as appropriate according to the size of the particle-like bodies 51 that flow into the monitoring portion 12. That is, if the maximum height (maximum internal diameter) h of the monitoring portion 12 is too large relative to the size (for example, the diameter) of the particle-like bodies 51, the probability that the particle-like bodies 51 will be present on top of one another (overlapping) inside the monitoring portion 12 increases and therefore the probability that it will not be possible to identify individual bodies in the plurality of particle-like bodies 51 increases. On the other hand, if the maximum height (maximum internal diameter) h of the monitoring portion 12 is too small relative to the size of the particle-like bodies 51, the monitoring portion 12 will provide resistance to passage of the particle-like bodies 51 and there is the possibility that it will be difficult for the particle-like bodies 51 to be smoothly discharged from the nozzle opening 11.

Accordingly, the maximum height (maximum internal diameter) h in the Y direction of the monitoring portion 12 and the average particle diameter (diameter) r of the particle-like bodies 51 to be identified should preferably satisfy the condition below.

$$1.2 \leq h/r \leq 100.0 \tag{1}$$

(h/r) should more preferably be 50.0 or below. Also, (h/r) should preferably be 1.4 or above and even more preferably 1.5 or above.

Also, the maximum height (maximum internal diameter) h in the Y direction of the monitoring portion 12 and the maximum height (maximum internal diameter) d in the Y direction of the nozzle opening 11 should preferably satisfy the condition below.

$$0.5 \leq h/d \leq 20.0 \tag{2}$$

(h/d) should more preferably be 15.0 or below. Also, (h/d) should more preferably be 0.8 or above.

Also, the maximum height (maximum internal diameter) d in the Y direction of the nozzle opening 11 and the maximum width b in the X direction of the nozzle opening 11 should preferably satisfy the condition below.

$$1.0 \leq b/d \leq 20.0 \tag{3}$$

(b/d) should more preferably be 10.0 or below.

One method of forming the first flattened portion 22 is to heat the glass tube 20 and then press the glass tube 20 in the up-down direction (a direction perpendicular to the length direction). By forming the glass tube 20 not in one dimension (the front-back direction or length direction) but in two dimensions (the up-down direction and a direction perpendicular to the length direction) with pressing the glass tube 20 in a state squeezed outward, the monitoring portion 12 that is internally provided with a flattened space is formed. In addition, a flat surface 22b is formed on the outside of the first side wall 22a of the first flattened portion 22 of the glass tube 20 and a flat surface 22d is formed on the outside of the first side wall 22c. This method of forming is one example, but it is also possible to mold the glass tube 20 into a predetermined shape by blowing a tubular member such as glass or resin into a mold as in injection molding, or by rolling metal to obtain a tubular member of a predetermine shape.

The first side wall 22a and the second side wall 22c may be flat or may be curved. If the walls are curved, the particle-like bodies 51 of the monitoring portion 12 will become easy to visually confirm due to a lens effect. On the other hand, if the first side wall 22a and the second side wall 22c are flat, if the maximum height (maximum internal diameter) h inside the monitoring portion 12 is uniform, it will be easy to obtain an image with little distortion through the side walls 22a and 22b which makes it easy to distinguish the type of the particle-like bodies 51 from the form of the particle-like bodies 51. Also, the box-like monitoring portion 12 is constructed by the flat side walls 22a and 22c, so that the particle-like bodies 51 can easily be uniformly dispersed in the X direction of the monitoring portion 12. Accordingly if a plurality of particle-like bodies 51 are present in the monitoring portion 12, it is easy to visually confirm or detect the particle-like bodies 51.

Figure 8:
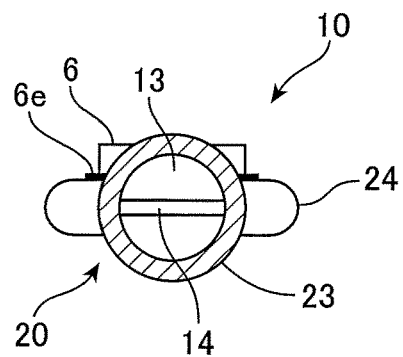
FIG. 8 is a cross-sectional view showing a cylindrical part of the discharge head.

The first cylindrical portion 23 that is to the rear of (next to) the first flattened portion 22 is a part that constructs a first connecting channel 13 for connecting (fluidly connecting) the monitoring portion 12 and the cavity 14. As shown by the enlarged cross section in FIG. 8, the first cylindrical portion 23 has high strength by its cylindrical shape, so that even if the cavity 14, described later, deforms due to the piezoelectric element 6, such change in form will have little effect on the first flattened portion 22. Note that in order to transmit changes in the internal pressure of the cavity 14 to the monitoring portion 12 and have the liquid material 50 in the monitoring portion 12 discharged from the nozzle opening 11, it is desirable for the internal cross-sectional area of the first cylindrical portion 23 to be substantially the same as the internal cross-sectional area of the monitoring portion 12. Also, instead of the first cylindrical portion 23, the cavity 14 and the monitoring portion 12 may be connected by a flattened part.

Figure 9:
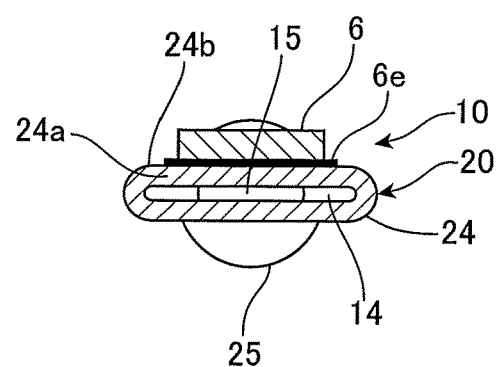
FIG. 9 is a cross-sectional view showing a different flattened part of the discharge head.

The second flattened portion 24 to the rear of (next to) the first cylindrical portion 23 has a flattened box-like space formed inside as the same way as the first flattened portion 22, and is a part that constructs the cavity 14 which is a pressure chamber. An enlargement of the cross-section of the second flattened portion 24 is shown in FIG. 9. The flat piezoelectric element (piezo element, actuator) 6 is attached to the surface (outer surface) 24b on the outside of the flat wall 24a of the cavity 14. The piezo element 6 is attached to the glass tube 20 together with a thin-film electrode 6e made of ITO, metal, or the like, receives driving pulses (voltage driving pulses) via the electrode 6e and expands and contracts to cause fluctuations in the internal volume of the cavity 14. Note that a piezoelectric element 6 is a typical pressure-electro conversion element and the piezo element 6 has a known construction that includes an electrode and the like.

The second cylindrical portion 25 to the rear of the second flattened portion 24 is a part that constructs a second connecting path 15 for connecting the cavity 14 and a narrow flow path 16 to the rear that functions as an orifice where the opening area is narrower. The connecting path 15 also functions as a buffer for supplying the liquid material 50 including the particle-like bodies 51 to the cavity 14.

Figure 10:
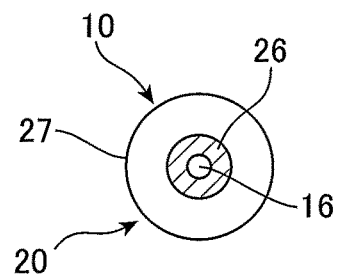
FIG. 10 is a cross-sectional view showing a narrowed part of the discharge head.

The narrowed part 26 to the rear of the second cylindrical portion 25 is a part that constructs the flow path 16 where the opening area is narrowed and an enlargement of the cross section of the narrowed part 26 is shown in FIG. 10. The inner diameter of the flow path 16 is 20 to 200 μm, for example, the pressure variation of the cavity 14 is effectively transmitted to the nozzle opening 11 side so that it is difficult for the pressure variation of the cavity 14 to propagate to the supply tube 4 and the vessel 5. One method of forming the narrowed part 26 is to pull the heated glass tube 20 in the front-rear direction (length direction). The third cylindrical portion 27 to the rear of the narrowed part 26 is a part that constructs a third connecting path 17 for connecting to the supply tube 4.

The front end part 21, the first flattened portion 22, the first cylindrical portion 23, and the second flattened portion 24 are formed by working (molding) the single glass tube 20. Accordingly, since it is possible to form the glass tube 20 seamlessly from the cavity to the nozzle opening, stagnation and/or blockages due to bubbles or the like hardly occur, so that it is possible to prevent the particle-like bodies 51 such as cells from adhering and prevent the stagnation of the flow of the liquid material 50 and blockages of the particle-like bodies 51 from the outset. For this reason, it is possible to provide the discharge head 10 that is suited to discharging a wide variety of particle-like bodies 51 and liquid materials 50, from low viscosity to high viscosity.

Note that although the glass tube 20 is used in the above description, in place of the glass tube 20, it is possible to form a resin tube or a ceramic tube that is light transmissive (transparent) into the same form and thereby provide a discharge head 10 that is seamless and is suited to measuring the number or the like of the particle-like bodies 51 at low cost.

In this way, since the discharge head 10 includes the flattened monitoring portion 12 to the rear of the nozzle opening 11 and the flattened monitoring portion includes the flattened nozzle opening 11, it is possible to detect the number and form of the particle-like bodies 51 included in the liquid material 50 to be discharged next or to be discharge laterfrom the nozzle opening 11 by the detection apparatus 7. On example of the detection apparatus 7 is shown in FIG. 4. The detection unit 7 includes a light source 101 disposed so as to face the first side wall 22a of the first flattened portion 22, an image pickup unit 102 disposed so as to face the second side wall 22c opposite the light source 101, and the image processing mechanism 103 that processes an image acquired by the image pickup unit 102. The light source 101 illuminates the particle-like bodies 51 present in the monitoring portion 12 and the particle-like bodies 51 included in the droplet 71 discharged from the nozzle opening 11. One example of the light source 101 is a so-called strobe light that is able to cyclically emit light, and as one example it is possible to use a halogen lamp such as a xenon lamp, an LED lamp, or a "black light" (ultraviolet light). It is desirable for the light source 101 to be capable of adjusting the luminance in keeping with the performance of the image pickup unit 102.

The image pickup unit 102 acquires an image, via the transparent second side wall 22c of the monitoring portion 12, including a state of the liquid material 50 illuminated by the light source 101 and the liquid material 50 discharged from the nozzle opening 11 toward the targets 81a to 81c. Accordingly, when particle-like bodies 51 are included in the liquid material 50 in the monitoring portion 12 and/or particle-like bodies 51 are included in the discharged liquid (droplet) 50, by analyzing the obtained image, it is possible to recognize the number and form of the particle-like bodies 51 included in the monitoring portion 12 and the number and form of the particle-like bodies 51 included in the discharged liquid material 50. An image pickup unit that acquires an image of the particle-like bodies 51 included in the liquid material 50 in the monitoring portion 12 and an image pickup unit that picks up an image of the liquid discharged from the nozzle opening 11 may be separately provided.

One example of the image pickup unit 102 is a camera equipped with an image pickup element (CCD, CMOS), and an optical lens. The optical lens is capable of adjusting the focal length and also changing the image pickup magnification and should preferably be capable of setting an image pickup magnification in a range where it is possible to simultaneously pick up an image of a plurality of minute particle-like bodies 51 included in the liquid material 50. The image processing mechanism 103 analyzes an image acquired by the image pickup element 102, and identifies the presence, number, and form of the particle-like bodies 51 in the monitoring portion 12 and the presence, number, and form of the particle-like bodies 51 in the droplets 71 after discharging. One example of the image processing mechanism 103 includes a parallel computational processing feature or configuration, and one example of the parallel computational processors is a high-speed image processor that has position computation elements each corresponding to each pixel of a CMOS sensor.

The monitoring portion 12 is flattened and is formed so as to be wider in the X direction and narrower in the Y direction than the first cylindrical portion 23. Accordingly, if a plurality of particle-like bodies 51 such as cells, included in the liquid material 50 are present in the monitoring portion 12, such particle-like bodies 51 will disperse and spread out in the X direction and tend to become present in a non-overlapping state between the first side wall 22a and the second side wall 22c. For this reason, in the discharge head 10, when a plurality of the particle-like bodies 51 are present in the monitoring portion 12, it is easy to separately detect the particle-like bodies 51 from outside the first side wall 22a and the second side wall 22c and to identify whether a plurality of the particle-like bodies 51 are present.

According to the discharge device 1 equipped with the discharge head 10, by observing the presence, number, and form of the particle-like bodies 51 in the monitoring portion 12 which is immediately above (immediately upstream) of the nozzle opening 11, it is possible using the detection apparatus 7 to identify whether particle-like bodies 51 are included in the liquid material 50 (the droplet 71) to be discharged next and also the included number of particle-like bodies 51 and the form (type) of the included particle-like bodies 51 before the liquid material 50 is discharged (dispensed) from the nozzle opening 11 and thereby obtain the detection result 7a. This means that with the discharge device 1, only the liquid material 50 that includes the particle-like bodies 51 of the desired number and form (type) is discharged onto one of the targets 81a to 81c and that in other cases, it is possible to agitate the liquid material 50 to change the state of the monitoring portion 12 and/or to dispose the liquid material 50 into the disposer 82 to change the state of the monitoring portion 12.

Therefore, according to the discharge device 1, it is possible to selectively discharge only a droplet 71 (which includes particle-like bodies) where the detection result 7a satisfies a predetermined condition onto the targets 81a to 81c. For this reason, when dispensing the droplets 71 including the particle-like bodies 51 onto a microplate (target) including a plurality of wells, it is possible to greatly reduce the presence of wasted wells that do not satisfy conditions of an experiment or the like.

Figure 11:
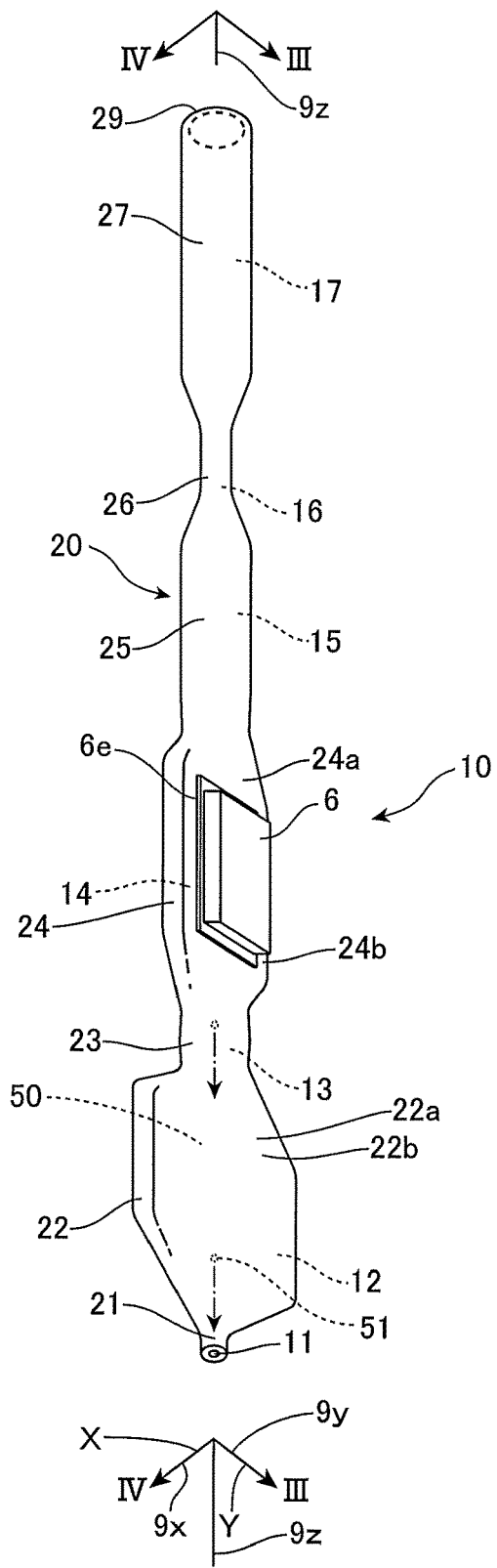
FIG. 11 is a perspective view showing a different example of a discharge head.

FIG. 11 shows a different example of a discharge head 10. The glass tube 20 of the discharge head 10 is equipped with the nozzle opening 11 that is cylindrical. At the front end part 21 of the glass tube 20 that forms the nozzle opening 11, the front end of the glass tube 20 is molded or formed into a narrowed shape of a suitable size as the nozzle opening 11. A typical internal diameter of the nozzle opening 11 is 15-200 μm.

In the discharge device 1 equipped with the discharge head 10 also, the presence and number of particle-like bodies 51 are observed at the monitoring portion 12 that is connected to and is immediately above (immediately upstream) of the nozzle opening 11. This means that it is possible before the liquid material 50 is discharged (dispensed) from the nozzle opening 11, to acquire, from the detection apparatus 7, a detection result 7a including whether particle-like bodies 51 are included in the liquid material 50 (the droplet 71) to be discharged next and the number, form, and the like of the included particle-like bodies 51. For this reason, in the discharge device 1, it is possible to discharge only the liquid material 50 including the particle-like bodies 51 of desired condition, that is, a predetermined number and/or form (type) onto a predetermined one of the targets 81a to 81c. When the detection result 7a does not match the desired condition, it is possible to agitate the liquid material 50 to change the state of the monitoring portion 12 and/or to dispose of the liquid material 50 into the disposer 82 to change the state of the monitoring portion 12. Since the remaining construction of the discharge head 10 is the same as the discharge head described above, description thereof is omitted.

Figure 12:
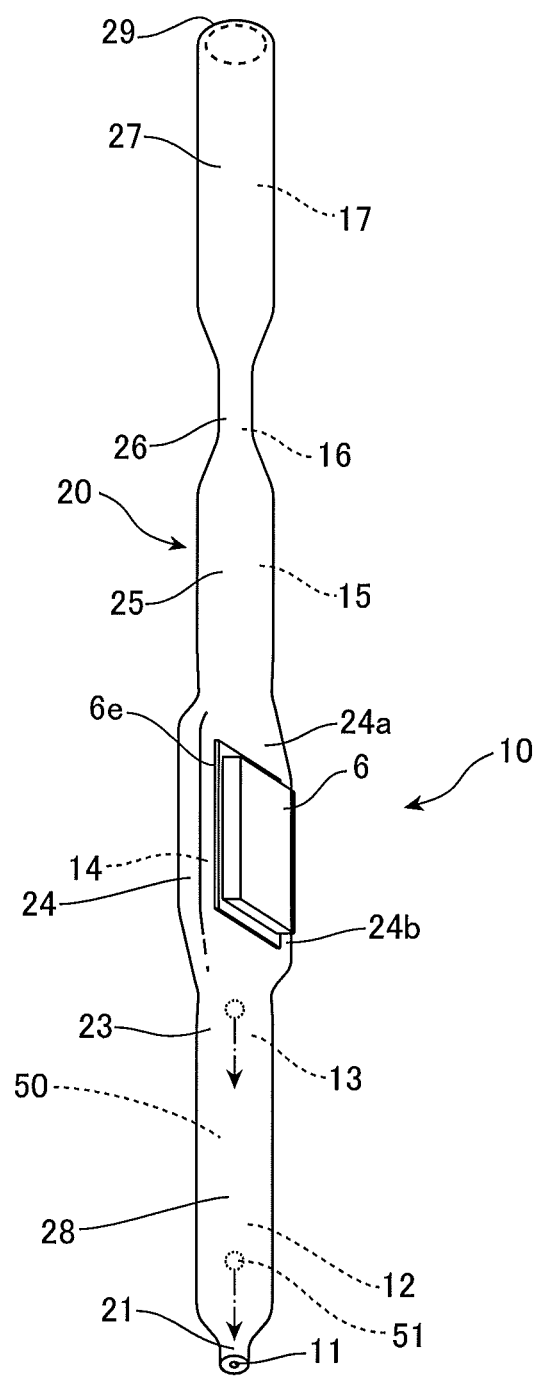
FIG. 12 is a perspective view showing yet another example of a discharge head.

FIG. 12 shows yet another example of the discharge head 10. The glass tube 20 of the discharge head 10 is equipped with a cylindrical monitoring portion 12. That is, the glass tube 20 includes a fourth cylindrical portion 28 that forms the monitoring portion 12 to the rear of the front end part 21 and in front of the first cylindrical portion 23. Accordingly, if the size of the particle-like bodies 51 is comparatively large and the particle diameter (diameter) r of the particle-like bodies 51 is 10 μm or above for example, it is possible to detect the particle-like bodies 51 by providing the fourth cylindrical portion 28 where the glass tube 20 is still cylindrical in place of the first flattened portion 22 where the glass tube 20 is molded by being squeezed from outside. Since the remaining construction of the discharge head 10 is the same as the discharge head described above, description thereof is omitted.

On the other hand, if the particle diameter (diameter) r of the particle-like bodies 51 is below 10 μm, since there is increased probability that the particle-like bodies 51 will be present on top of one another (overlapping each other) inside the monitoring portion 12 and increased probability that it will not be possible to distinguish individual particle-like bodies 51 out of the plurality of particle-like bodies 51, it is preferable to provide the first flattened portion 22 formed by squeezing the glass tube 20 from outside. If the particle diameter (diameter) r of the particle-like bodies 51 is 5 μm or below, it is even more preferable to provide the first flattened portion 22.

Figure 13:
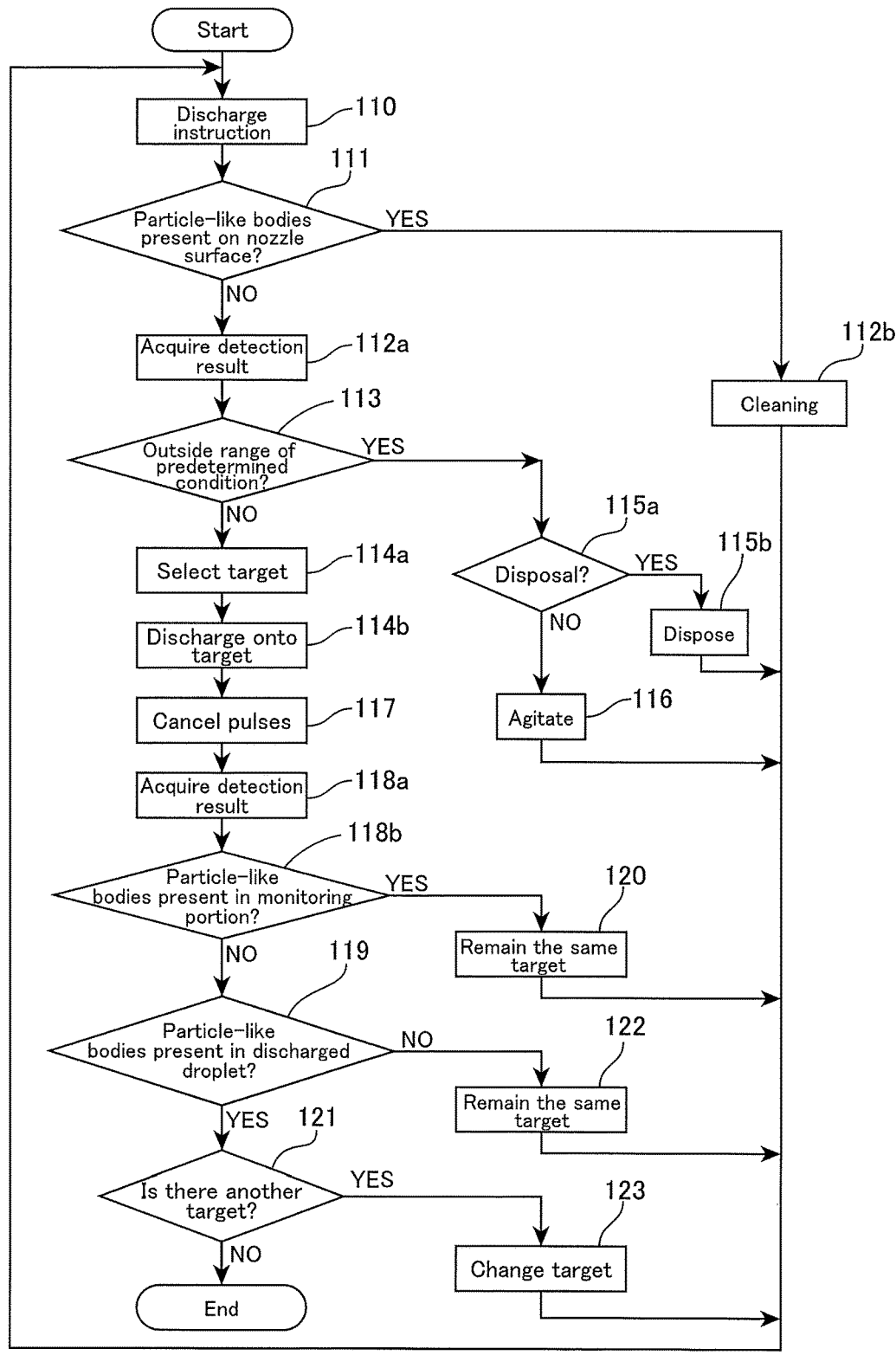
FIG. 13 is a diagram showing a flowchart of the discharging method according to the present invention.

FIG. 13 shows, by way of a flowchart, a method (a control method of the discharge device 1) of discharging a droplet 71 including particle-like bodies 51 according to a predetermined condition onto one of the targets 81a to 81c using the discharge device 1 equipped with the discharge head 10.

Figure 5:
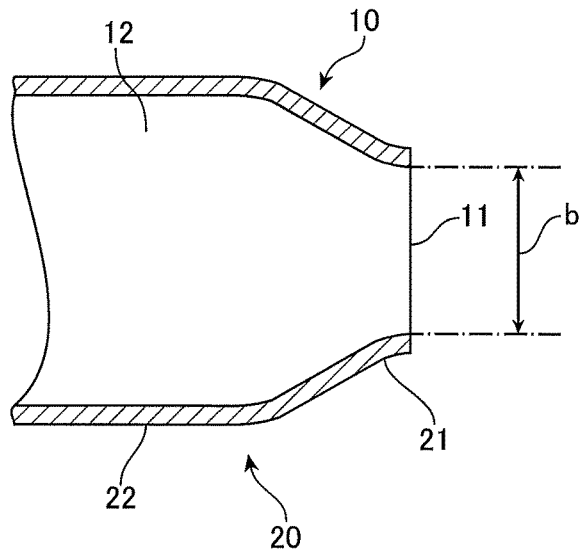
FIG. 5 is a cross-sectional view showing an enlargement of the front end of the discharge head.
Figure 6:
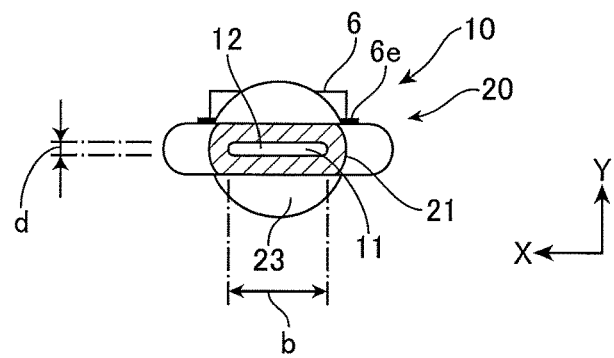
FIG. 6 is a cross-sectional view showing a front-end part of the discharge head.

If, in step 110, a discharge instruction has been outputted from the host apparatus, in step 111 the control unit 74 uses an image of a nozzle surface 11a of the nozzle opening 11 obtained from the detection apparatus 7 to determine whether particle-like bodies 51 are present on the nozzle surface 11a of the nozzle opening 11 shown in FIG. 5. If particle-like bodies 51 or other foreign matter is present at the nozzle surface 11a, the control unit 74 switches to cleaning mode (wiping mode) in step 112b. If the particle-like bodies 51 or other foreign matter is present at the nozzle surface 11a, the flying direction of the droplet 71 discharged from the discharge head 10 will change and there is the possibility that the droplet 71 will not reach the desired target. Accordingly, it is first confirmed whether the nozzle surface 11*a* is clean, and if foreign matter is present, the nozzle surface 11*a* is cleaned.

In cleaning mode, the actuator 79 and/or 89 is used to move the discharge head 10 to the home position and the nozzle surface 11*a* is cleaned using a wiping mechanism or the like provided at the home position to remove the foreign matter. In cleaning mode, the discharge head 10 may move to the disposer 82 and the particle-like bodies 51 or the foreign matter present at the nozzle surface 11*a* may be removed by disposing of the droplet (i.e., cleaning).

After the cleaning in step 112*b* ends, the control returns to step 110, it is confirmed that a discharge instruction is held, and the discharge process described below continues. After the cleaning in step 112*b* has ended, the control may return to step 111 without confirming the discharge instruction to confirm once again whether foreign matter is present on the nozzle surface 11*a* and then continue the discharge process described below.

If particle-like bodies 51 are not detected at the nozzle surface 11*a*, in step 112*a* an acquisition unit 75 of the control unit 74 acquires the detection result 7*a* including information on the number and/or form (for example, the size (diameter), shape, pattern and color) of the particle-like bodies 51 included in the liquid material 50 in the monitoring portion 12 from the detection unit 7. In step 113, if a condition such as the number and/or form or the like of the particle-like bodies 51 included in the detection result 7*a* is within a range of a predetermined condition, in step 114*a* the discharge target changing unit 78 of the state changing unit 76 selects one of the targets 81*a* to 81*c* and in step 114*b* moves the discharge head 10 to one of the targets 81*a* to 81*c* that matches the predetermined condition using the actuator 79 and/or 89 and uses the driving unit 2 to discharge the liquid material 50 onto the designated target 81.

On the other hand, if the acquired detection result 7*a* is not within the range of the predetermined condition, in step 115*a* the state changing unit 76 determines whether to dispose of the liquid material 50. If the liquid material 50 is to be disposed of, in step 115*b*, a disposal unit 78*a* of the discharge target changing unit 78 moves the discharge head to the disposer 82 using the actuator 79 and/or 89 and disposal is carried out using the driving unit 2. After this, the control returns to step 110.

If the liquid material 50 is not to be disposed of, in step 116, an agitation unit 77 controls a driving voltage applied to the piezoelectric element (piezo element) 6 from the driving unit 2 to change or fluctuate the internal pressure of the cavity 14 to an extent where a droplet is not discharged, thereby agitating the liquid material 50 and changing the state of the monitoring portion 12, then the control returns to step 110.

By selecting agitation in step 116, it is possible to change the distribution and position of the particle-like bodies 51 in the monitoring portion 12 without disposing of the particle-like bodies 51. This means that it is possible to greatly reduce the presence (amount) of the particle-like bodies 51 that is wasted and it is also unnecessary to move the discharge head 10 or the table 83 using the actuator 79 and/or 89 to carry out disposal.

The decision whether to select disposal in step 115*b* or to select agitation in step 116 may be set in advance as an initial setting of the state changing unit 76 or disposal may be selected when a detection result 7*a* that matches a predetermined condition has not been obtained in spite of agitation being repeated a number of times. It is also possible to select agitation or disposal by determining, according to the detection result 7*a*, whether it is possible to change the state of the monitoring portion 12 so as to match the predetermined condition by selecting agitation in step 116.

When a droplet 71 is discharged onto one of the targets 81*a* to 81*c* in step 114*b* or the liquid material 50 is disposed of in step 115*b*, the control unit 74 drives the piezoelectric element 6 via the driving apparatus 2 with drive pulses for a "pushing" type (method), not drive pulses for a "pulling" type (method). Here, the expression "pulling type" refers for example to applying a voltage to the piezoelectric element 6 in a normal state to keep the cavity 14 in a state with a reduced volume, reducing the applied voltage immediately before discharge to increase the volume of the cavity 14 and then applying a voltage once again to reduce the volume of the cavity 14 and discharge a droplet 71. On the other hand, the expression "pushing type" refers to having no voltage applied to the piezoelectric element 6 in a normal state and applying a voltage when discharging a droplet 71 to cause the piezoelectric element 6 to deform and increase the pressure in the cavity 14, thereby discharging a droplet 71.

Since the meniscus of the nozzle opening 11 will be pulled in if the pulling type pulses are used, the meniscus may be pulled in as far as inside the monitoring portion 12, which varies the internal state of the monitoring portion 12. This means that the state of the monitoring portion 12 that was confirmed in step 113 may change and unexpected particle-like bodies 51 will be included in the droplet 71 that is discharged. On the other hand, with the pushing type pulses, since the meniscus of the nozzle opening 11 is hardly pulled in, the state of the monitoring portion 12 will not be varied and it will be possible to discharge a droplet 71 including the expected particle-like bodies 51.

Immediately after supplying drive pulses for the pushing method to the piezoelectric element 6 in step 114*b*, the driving unit 2 supplies pulses that cancel movement of the meniscus to the piezoelectric element 6 in step 117. By causing rapid attenuation of the vibration of the meniscus and suppressing movement of the meniscus to a minimum, it is possible to quickly stabilize the internal state of the monitoring portion 12.

If, in step 114*b*, the particle-like bodies 51 of the indicated condition have been discharged on the indicated target 81*a* to 81*c*, in step 118*a* the acquisition unit 75 of the control unit 74 acquires an image of the droplet immediately after discharge and a detection result 7*a* for the monitoring portion 12 after discharge from the detection apparatus 7.

In step 118*b*, if particle-like bodies 51 that satisfy the conditions before discharge are present in the detection result 7*a* after discharge, the control unit 74 determines that a droplet 71 including the particle-like bodies 51 has not been discharged. If the liquid material 50 may be repeatedly discharged onto the desired target 81*a* to 81*c*, in step 120 the control returns to step 110 without changing the target, the conditions are confirmed again in steps 111 and 113, and then discharging is repeated in step 114*b*.

If the particle-like bodies 51 that satisfy the conditions before discharge are not present in the detection result 7*a* after discharge, in step 119 the control unit 74 uses the image of the discharged droplet to determine whether particle-like bodies 51 of predetermined conditions were included in the discharged droplet. If particle-like bodies 51 are not detected in the discharged droplet 71, the control unit 74 determines that a droplet 71 including the particle-like bodies 51 has not been discharged on the desired target 81*a* to 81*c*. If the liquid material 50 may be repeatedly discharged onto the desired target 81a to 81c, in step 122 the control returns to step 110 without changing the target 81, the conditions are confirmed again in steps 111 and 113 and then discharging is repeated in step 114b.

At the same time as step 118b or at around the same time, by confirming in step 119 that the particle-like bodies 51 are included in the droplet 71 after discharge, the possibility of particle-like bodies 51 adhering to the nozzle surface 11a and not being discharged onto the target 81 is detected so that it becomes possible to reliably discharge the particle-like bodies 51.

If in step 121 there is another target, in step 123 there is a change to another target and the control returns to step 110. If there is no other target in step 121, the control ends.

Figure 14:
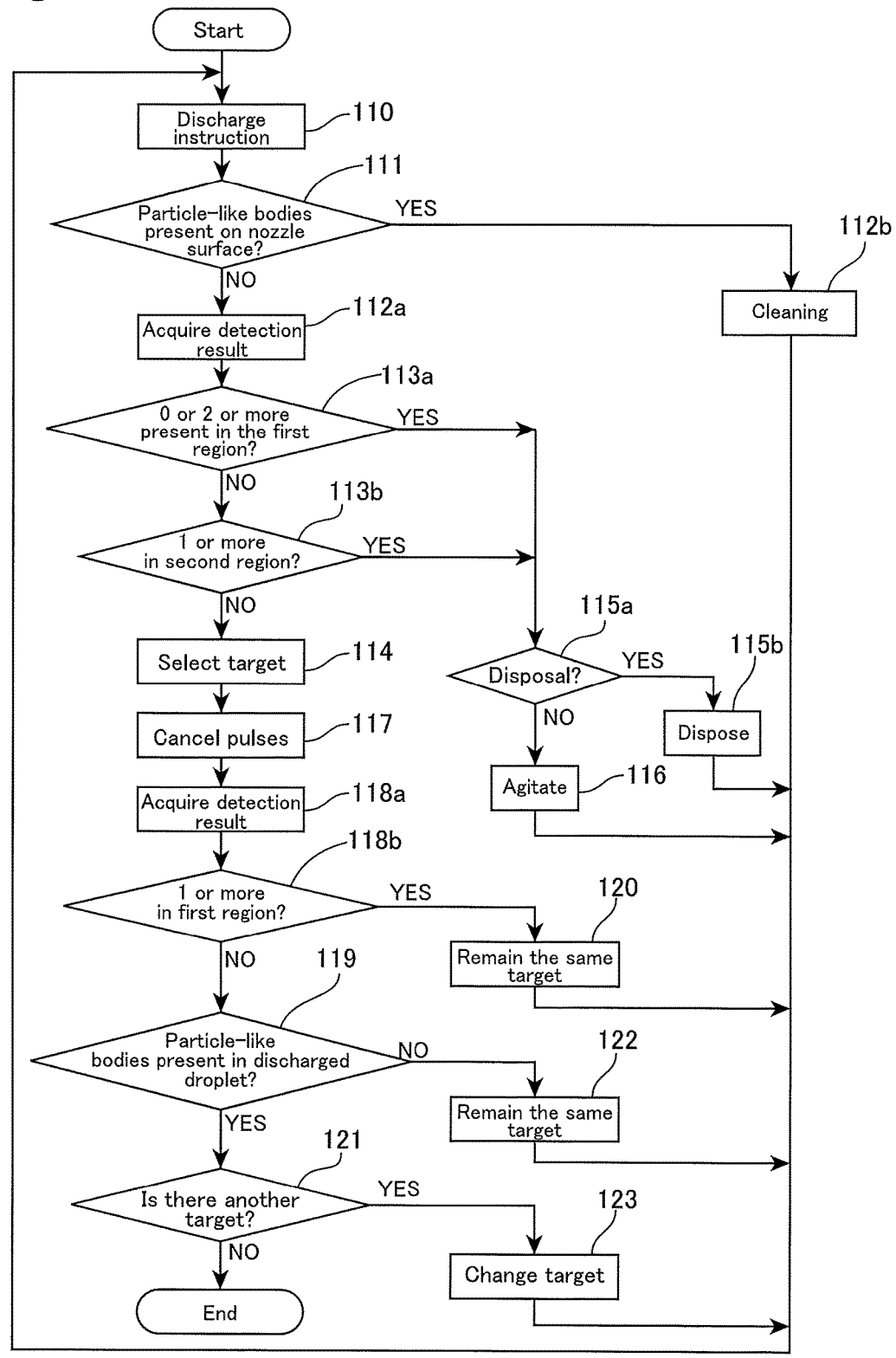
FIG. 14 is a diagram showing a flowchart of another discharging method according to the present invention.

FIG. 14 shows one example of an algorithm for a case where a droplet 71 including only one particle-like body 51 is discharged onto a target 81. In this algorithm, the control unit 74 of the discharge device 1 uses the detection apparatus 7, the driving apparatus 2 for controlling the piezo element 6 and the second actuator 79 and/or the third actuator 89 for movement Note that description is omitted for steps that are the same as the flowchart described above.

Figure 15:
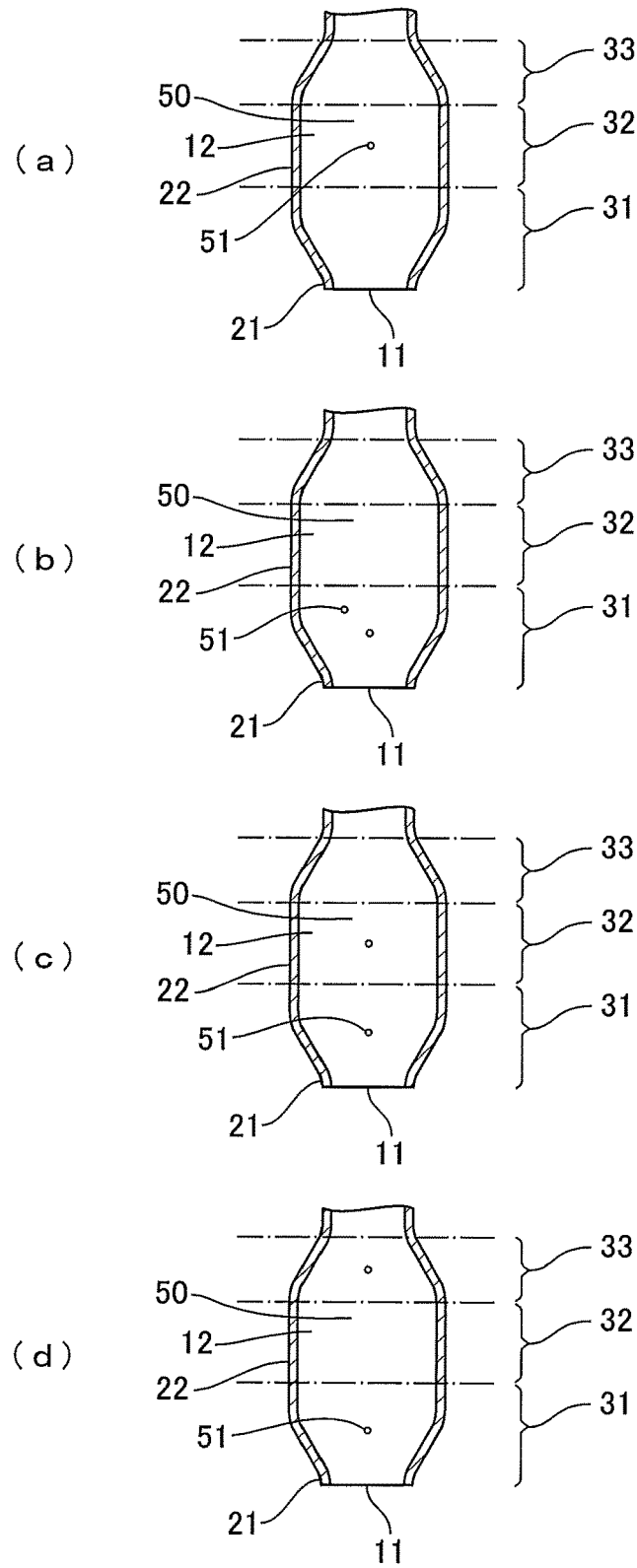
FIG. 15 is a series of cross-sectional views showing an enlargement of a flattened part of a discharge head, with (a) to (c) as diagrams schematically showing states where liquid material is agitated or disposed of and (d) as a diagram schematically showing a state where the liquid material is discharged onto a target.

FIG. 15 shows the state of the monitoring portion 12. In this example, as shown in FIG. 15, the monitoring portion 12 has a volume that holds an amount equivalent to three discharges and the inside of the monitoring portion 12 is ideally or virtually divided into a part (first region) 31 to be discharged next from the nozzle opening 11, a part (second region) 32 to be discharged after that (i.e., second), and a part (third region) 33 to be discharged after that (i.e., third). Although the monitoring portion 12 of the discharge head 10 is shown in FIG. 15 as being clearly separated into these regions 31 to 33 from the nozzle opening 11 at the front end to the rear end 29, such regions are virtual regions set for image analysis and the form of the boundaries of the regions 31 to 33 are not limited to this example.

If, in step 110, a discharge instruction has been outputted from the host apparatus, in step 111 the control unit 74 determines whether the particle-like bodies 51 have been detected at the nozzle surface 11a of the nozzle opening 11. If no particle-like bodies 51 have been detected at the nozzle surface 11a, in step 112a, the acquisition unit 75 of the control unit 74 acquires the detection result 7a including information on the individual particle-like bodies 51 included in the liquid material 50 of the monitoring portion 12 from the detection apparatus 7.

In step 113a, if no particle-like bodies 51 have been detected (zero detection) or two or more particle-like bodies 51 have been detected in the first region 31 closest to the nozzle opening 11 in the monitoring portion 12, the state changing unit 76 determines whether to dispose of the liquid material 50 in step 115a. If the liquid material 50 is to be disposed of, in step 115b, the disposal unit 78a of the discharge target changing unit 78 points the nozzle opening 11 at the disposer 82 using the actuator 79 and/or 89, carries out disposal using the driving unit 2, and the control returns to step 110. If the liquid material 50 is not to be disposed of, in step 116 the agitation unit 77 agitates the liquid material 50 with an amount of pressure that does not cause discharge to change the state of the monitoring portion 12 and the control returns to step 110.

FIG. 15(a) shows a case where zero particle-like bodies 51 are detected, that is, particle-like bodies 51 are not detected, in the first region 31. FIG. 15(b) shows a case where two particle-like bodies 51 are present in the first region 31. The first region 31 holds liquid material 50 to be discharged next from the nozzle opening 11 and if zero or two or more particle-like bodies 51 are present in the first region 31, by disposing of or agitating the liquid material 50 in step 115 and 116, it is possible to prevent the failure of a particle-like body 51 to enters the target 81 or the supplying of two or more particle-like bodies 51.

At the same time as step 113a or at around the same time, if in step 113b one or more particle-like bodies 51 is measured in the second region 32 which is to be discharged after the first region 31, the state changing unit 76 determines in step 115a whether to dispose of the liquid material 50. If the liquid material 50 is to be disposed of, in step 115b the disposal unit 78a points the nozzle opening 11 at the disposer 82 using the actuator 79 and/or 89, carries out disposal using the driving unit 2, and the control returns to step 110. If the liquid material 50 is not to be disposed of, in step 116 the agitation unit 77 agitates the liquid material 50 with an amount of pressure that does not cause discharge to change the state of the monitoring portion 12 and the control returns to step 110.

FIG. 15(c) shows a state where one particle-like body 51 is present in the first region 31 and one particle-like body 51 is also present in the second region 32. If particle-like bodies 51 are present in the second region 32 that is adjacent to the first region 31, there is the possibility of the particle-like bodies 51 in the second region 32 being discharged together with the particle-like bodies 51 in the first region 31 in the next discharge, which would result in a droplet 71 including two particle-like bodies 51 being discharged onto the target 81 in the next. In this case, the second region 32 is used as a buffer region and if a particle-like body or particle-like bodies 51 are included in the second region 32, the liquid material 50 is agitated or disposed of to change the state of the monitoring portion 12 and further improve the discharge precision.

If, in steps 113a and 113b, a condition for agitating or disposing of the liquid material 50 is not satisfied, in step 114 the discharge target changing unit 78 of the state changing unit 76 uses the actuator 79 and/or 89 to point the nozzle opening 11 at the target 81 and discharges the liquid material 50 in the first region 31 onto the target 81 using the driving unit 2. The case where a condition for agitating or disposing of the liquid material 50 is not satisfied in steps 113a and 113b refers to a case where only one particle-like body 51 is detected in the first region 31 and no particle-like bodies 51 are detected in the second region 32. FIG. 15(d) shows one example of this state. Since only one particle-like body 51 is present in the region including the first region 31 and the second region 32 which is the buffer region, a droplet 71 including only one particle-like body 51 will be discharged toward the target 81 in step 114.

After the particle-like body 51 has been discharged, in step 118a the acquisition unit 75 of the control unit 74 acquires an image of the droplet immediately after discharge and the detection result 7a for the monitoring portion 12 after discharge from the detection apparatus 7. In step 118b, it is determined whether a particle-like body 51 has been detected in the first region 31. If a particle-like body 51 has not been detected in the first region 31, in step 119 the control unit 74 uses an image of the discharged droplet to determine whether a particle-like body 51 is detected in the discharged droplet 71. On the other hand, if a particle-like body 51 is detected in the first region 31, the control unit 74 determines that a droplet 71 with a particle-like body 51 has not been discharged. In a case where the discharging of liquid material 50 onto the target 81 may be repeated, in step 120 the control returns to step 110 without changing the target 81, the conditions of the monitoring portion 12 are confirmed again in step 113a and 113b, and discharging is carried out again in step 114.

If, in step 119, a particle-like body 51 has been detected in the discharged droplet 71, the control unit 74 determines that a droplet 71 of a predetermined condition, that is, a droplet 71 that includes one particle-like body 51 has been discharged onto the target 81 and in step 121 determines whether there is another target 81 onto which a particle-like body 51 is to be discharged. On the other hand, if a particle-like body 51 has not been detected in the discharged droplet 71, the control unit 74 determines that a droplet 71 that includes a particle-like body 51 has not been discharged onto the target 81. In a case where the discharging of liquid material 50 onto the target 81 may be repeated, in step 122 the control returns to step 110 without changing the target 81, the conditions of the monitoring portion 12 are confirmed again in step 112, and discharging is carried out again in step 114.

If, in step 121, there is another target, in step 123 the target is changed to the other target and the control returns to step 110. If, in step 121, there is no other target, the control ends.

If the discharging of liquid material 50 may be repeated, the volume Q1 of the first region 31 should preferably satisfy Condition (A) below relative to the volume q of a droplet 71 discharged from the nozzle opening 11.

$$1 \leq Q1/q \leq 1000 \quad (A)$$

Also, the volume Q2 of the second region 32 should preferably satisfy Condition (B) below.

$$0 \leq Q2/q \leq 1000 \quad (B)$$

If the concentration of the particle-like bodies 51 in the liquid material 50 is sufficiently low or the volume Q1 of the first region 31 is large relative to the volume q of the droplet 71, the second region 32 does not need to be provided and step 112b can be omitted.

In the case of Condition (A) above, the particle-like bodies 51 present in the first region 31 are discharged onto the target 81 or disposed of in Q1/q discharges. Accordingly, in step 114 and 115, the control may return to step 110 and confirm the state of the monitoring portion 12 after each discharge or may return to step 110 after a maximum of Q1/q discharges.

In addition, when the state before discharge does not satisfy the condition and the liquid material 50 is to be disposed of in step 115, if the concentration of the particle-like bodies 51 relative to the volume of the liquid material 50 in a single discharge is too high, the number of particle-like bodies 51 that are disposed of will increase, which can easily result in high cost. On the other hand, if the concentration of the particle-like bodies 51 relative to the volume of the liquid material 50 per single discharge is too low, the number of times disposal will be carried out until the number of particle-like bodies 51 matches the predetermined condition increases, which makes it difficult to reduce the time required to discharge onto the target 81.

Accordingly, it is preferable to discharge a droplet 71 with the volume q that satisfies the condition below in each single discharge from the nozzle opening 11.

$$0.0001 \leq D \times q \leq 3.0 \quad (5.0)$$

where D is the number of particle-like bodies 51 included per unit volume of the liquid material 50. (D×q) should more preferably be 2.0 or below or even more preferably 1.0 or below. Also, (D×q) should more preferably be 0.001 or above or even more preferably 0.01 or above.

Figure 16:
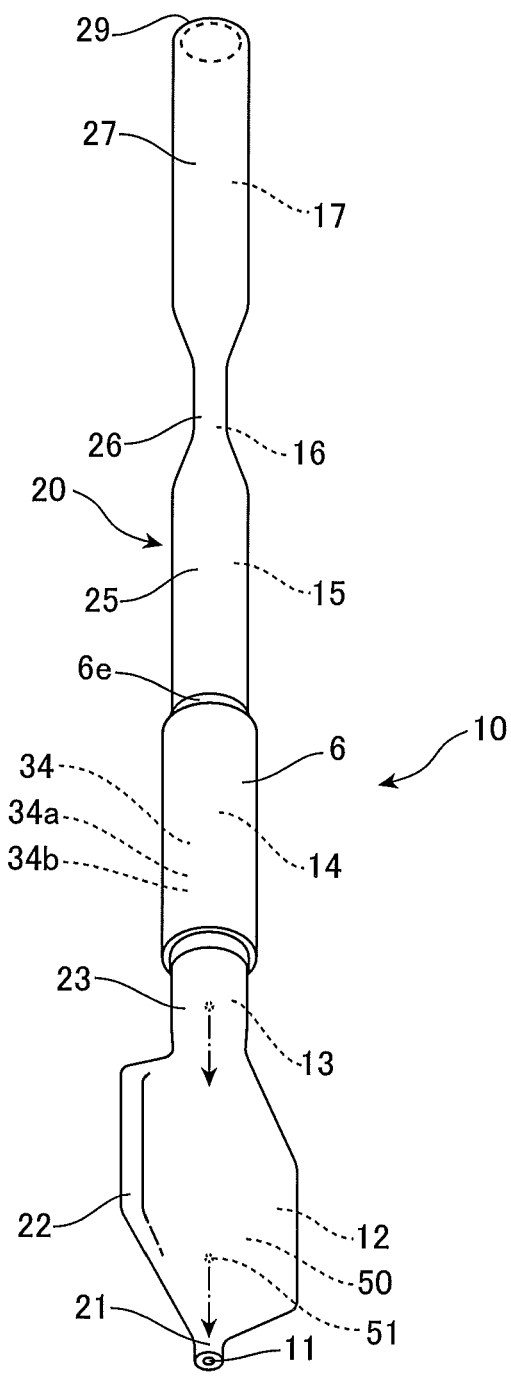
FIG. 16 is a perspective view showing yet another example of a discharge head.

FIG. 16 shows yet another example of the discharge head 10. The glass tube 20 of this discharge head 10 is equipped with a cylindrical cavity 14. That is, the glass tube 20 includes a fifth cylindrical portion 34 that forms the cavity 14 to the rear of the first cylindrical portion 23 and in the front of the second cylindrical portion 25. The piezoelectric element 6 that is cylindrical is attached via an electrode 6e to a surface (outer surface) 34b on the outside of the cylindrical wall 34a of the cavity 14. Accordingly, even in a so-called Gould-type discharge head 10 where the glass tube 20 and the cylindrical piezoelectric element 6 are combined, it is possible to provide a monitoring portion 12 for detecting the particle-like bodies 51 between the cavity 14 and the nozzle opening 11. Since the remaining construction of the discharge head 10 is the same as the discharge head described above, description thereof is omitted. In this way, by providing the monitoring portion 12 between the cavity 14 and the nozzle opening 11 regardless of the construction of the cavity 14, it is possible to selectively discharge a droplet 71 that includes particle-like bodies 51 according to a predetermined condition onto the target 81.

It is also possible to use a thermal-type ink jet method where a heater is attached to the glass tube 20 of the discharge head 10 in place of the piezoelectric element 6 and the internal pressure of the cavity 14 is varied using bubbles. Also, although one example of a control algorithm of the control unit 74 based on an example that discharges a droplet 71 including one particle-like body 51 has been explained in the above description, the algorithm may discharge droplets 71 that include n (where n is an arbitrary integer) particle-like bodies 51.

Figure 17:
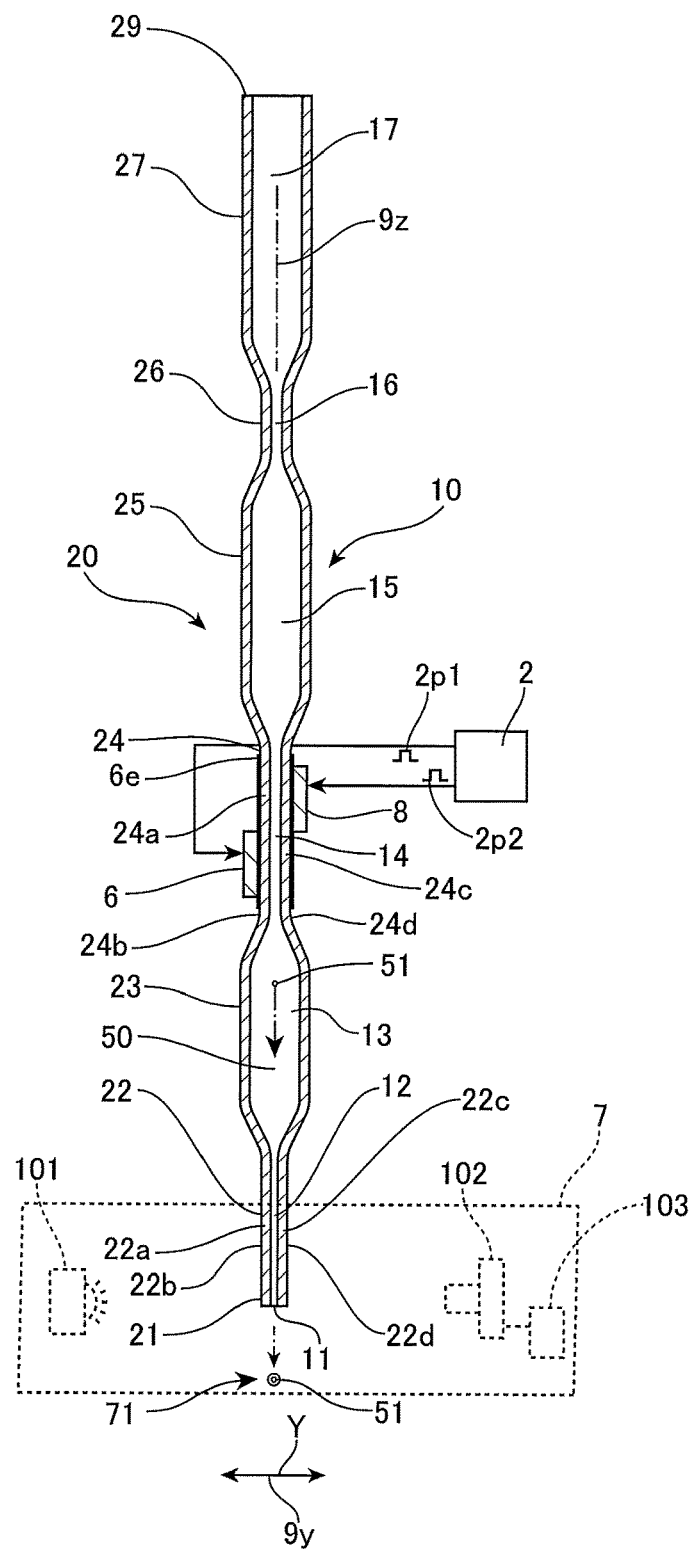
FIG. 17 is a cross-sectional view showing yet another example of a discharge head.

FIG. 17 shows yet another example of the discharge head 10 by way of a cross-sectional view. The cavity 14 of the discharge head 10 is molded into a state where the walls on both sides are narrowed and a second wall 24c with an outer surface 24d that is flat on the opposite side is provided at a position that faces (i.e., is opposite) the first wall 24a with the flat outer wall 24b onto which the piezo element 6 is attached. In the discharge head 10, a second piezo element 8, which is driven independently of the piezo element (first piezo element) 6 attached to the first wall 24a, is attached to the outer surface 24d of the second wall 24c at a position that is shifted so as to not be opposite the first piezo element 6 in the Y direction. It is possible to supply drive pulses 2p1 and 2p2 with different timing, pulse widths, pulse heights, and the like from the driving unit 2 to the first piezo element 6 and the second piezo element 8 respectively.

Figure 18:
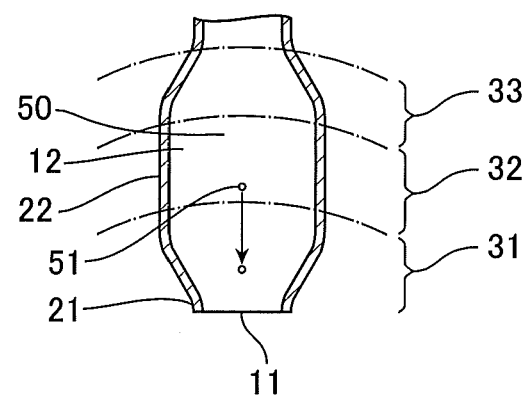
FIG. 18 is a cross-sectional view showing an enlargement of a flattened part of the discharge head shown in FIG. 17.

For example, by supplying the drive pulses 2p1 and 2p2 with different timing or changing the time for which the piezo elements 6 and 8 deform (are displaced) by the drive pulses 2p1 and 2p2, it is possible to produce a travelling wave that propagates from the cavity 14 toward the nozzle opening 11 with the liquid material 50 held inside the discharge head 10 as the medium. Accordingly, as shown in FIG. 18, it is possible to move the particle-like bodies 51 present in the second region 32 toward the first region 31 and further onto the nozzle opening 11 using the travelling wave. Note that the first piezoelectric element 6 and the second piezoelectric element 8, may be attached to the first wall 24a and the second wall 24c so as to face one another in the Y direction or may be attached to one of the first wall 24a and the second wall 24c at positions that are shifted in the length direction 9z.

Note that as shown in FIG. 18, the regions 31 to 33 inside the monitoring portion 12 may be separated from one another in a radial fashion (i.e., in a bow shape) from the nozzle opening 11 toward the cavity 14. Although the regions 31 to 33 are set so as to have convex boundaries from the nozzle opening 11 toward the cavity 14, it is also possible to set convex boundaries from the cavity 14 toward the nozzle opening 11. The shapes of the boundaries 31 to 33 can be changed as appropriate according to the discharge method such as the pushing method or the pulling method or according to conditions such as the shape or the like of the monitoring portion 12 and/or the nozzle opening 11.

Note that the targets for discharging the particle-like bodies 51 and the liquid material 50 include well-known experimental and testing equipment, such as a microplate (well microplate), a glass plate, a test tube, or a petri dish, and analysis equipment such as a DNA microarray (DNA chip) where a large number of DNA fragments are disposed with a high density on a plate made of plastic, glass, or the like.

Although an example that uses an actuator as a piezo element has been explained in the above description, the actuator that varies the internal pressure of the cavity may be a heater that produces bubbles inside the cavity using heat. However, a piezo element is preferable as the actuator since a piezo element is capable of changing the pressure inside the cavity using mechanical force with little thermal effect on the liquid and the particle-like bodies included therein. In addition, although the actuator is driven by drive pulses for the pushing method in the above description, the pulling method may be used. The pushing method can suppress pulling in of the meniscus at the nozzle opening as far as the monitoring portion, which makes it easier to stabilize the state of the monitoring portion 12. This means that when liquid including particle-like bodies that match a predetermined condition is discharged, a drop in discharge precision due to the inclusion of an unexpected number of particle-like bodies can be suppressed.

The invention claimed is:

1. A discharge device comprising:
   a discharge head comprising a cavity, a monitor, and a nozzle opening, wherein the cavity is upstream of the monitor, and the monitor includes the nozzle opening, such that the nozzle opening connected to the cavity via the monitor;
   an actuator that deforms a wall of the cavity to fluctuate an internal volume of the cavity and change an internal pressure of the cavity to supply a liquid material to the monitor and cause the liquid material to be discharged;
   the discharge device discharges the liquid material as a plurality of individual droplets from the nozzle opening, the monitor configured to hold the liquid material to be discharged as a next one of the plurality of droplets from the nozzle opening;
   a detection apparatus that detects a condition of particle bodies included in the liquid material immediately before discharge from the nozzle opening at the monitor, wherein the condition includes a number of the particle bodies in a droplet to be discharged next from the nozzle opening and the detection apparatus is configured to pick-up an image through a light transmissive part of the monitor to detect the condition as a detected condition; and
   a control apparatus that selectively controls the discharge device in two modes depending on the detected condition, when the detected condition is within a predetermined range, the actuator fluctuates the internal pressure, upstream of the monitor, in a range that causes the liquid material to be discharged from the nozzle opening as an individual droplets to a designated target, and in a second of the two modes, when the detected condition is not within the predetermined range, the control apparatus either agitates the liquid material or causes the individual droplet to be disposed from the discharge device.

2. The discharge device according to claim 1, wherein the monitor includes a flattened portion where a cross section of a flow path from the cavity to the nozzle opening of the discharge head extends to form oblate in a first direction, the flattened portion dispersing the particle bodies in the first direction.

3. The discharge device according to claim 2, wherein the nozzle opening is flattened so as to extend in the first direction.

4. The discharge device according to claim 1, wherein the control apparatus includes a function that changes a discharge target of the liquid material according to the detection result.

5. The discharge device according to claim 1, wherein the monitor includes a first region that is connected to the nozzle opening and a second region that follows the first region, the detection apparatus acquires a condition in the first region of the monitor as a first detected condition and a condition in the second region as a second detected condition, and the control apparatus is operable, when the first detected condition is outside a range of a first predetermined condition or when the second detected condition is outside a range of a second predetermined condition, to select the second of the two mode.

6. The discharge device according to claim 1, wherein the actuator is a piezo element, and the control apparatus includes a feature that supplies drive pulses of a pushing type to the piezo element when the liquid material is to be discharged.

7. The discharge device according to claim 1, wherein the monitor includes a first side wall and a second side wall that are flat and disposed facing one another.

8. The discharge device according to claim 1, further comprising a tubular member that holds the liquid material and part of which is shaped so as to form the cavity whose internal pressure is varied by the actuator attached to an outside of the tubular member, the nozzle opening being provided at one end of the tubular member, wherein the monitor is provided between the cavity and the nozzle opening of the tubular member.

9. The discharge device according to claim 8, wherein the monitor is a part molded by squeezing part of the tubular member from the outside.

10. The discharge device according to claim 8, wherein the tubular member is one of a glass tube, a resin tube, and a ceramic tube that is light transmissive.

11. A method of discharging a liquid material including particle bodies onto a target using a discharge device, wherein the discharge device includes a discharge head comprising a cavity, a monitor, and a nozzle opening, wherein the cavity is upstream of the monitor, and the monitor includes the nozzle opening, such that the nozzle opening connected to the cavity via the monitor, and an actuator that deforms a wall of the cavity to fluctuate an internal volume of the cavity and change an internal pressure of the cavity to supply the liquid material to the monitor and cause the liquid material to be discharged;

the discharge device discharges the liquid material as a plurality of individual droplets from the nozzle opening, the monitor configured to hold the liquid material to be discharged as a next one of the plurality of droplets from the nozzle opening, the method comprising:

acquiring a detection result, from the monitor, including a condition of the particle bodies included in the liquid material immediately before discharge from the nozzle opening at the monitor; wherein the condition includes a number of the particle bodies in a droplet to be discharged next from the nozzle opening by an image picked-up through a light transmissive part of the monitor as a detected condition and selectively controlling the discharge device in two modes depending on the detected condition, wherein in a first of the two modes, when the detected condition is within a predetermined range, the actuator fluctuates an internal pressure, upstream of the monitor, in a range that causes the liquid material to be discharged from the nozzle opening as an individual droplets to a designated target, and in a second of the two modes, when the detected condition is not within the predetermined range, either agitating the liquid material or causing the individual droplet to be disposed from the discharge device.

12. The method according to claim 11, wherein the controlling step includes changing a discharge target of the liquid material according to the detection result.

13. The method according to claim 11, wherein the acquiring the detection result includes setting, in the monitor, a first region that is connected to the nozzle opening and a second region that follows the first region, and acquiring a condition the first region as a first detected condition and a condition of the second region as a second detected condition, and the controlling includes selecting the second of the two mode when the first detected condition is outside a range of a first predetermined condition or when the second detected condition is outside a range of a second predetermined range.

14. The method according to claims 11, wherein the actuator is a piezo element, and the method comprises the control apparatus supplying drive pulses of a pushing type to the piezo element when the liquid material is to be discharged.

15. The method according to claim 11, wherein the discharge device includes an apparatus that picks up an image of a droplet discharged from the nozzle opening and carries out image analysis, and the method further comprises the apparatus that carries out image analysis determining whether the particle bodies are included in the droplet discharged from the nozzle opening.

16. The discharge device according to claim 1, wherein in the second of the two modes, when a predetermined condition is not detected by the monitor, the control apparatus causes the liquid material to be disposed from the discharge device.

17. The discharge device according to claim 1, wherein the detecting apparatus detects a number or forms of particle bodies as the detected condition of the particle bodies.

18. The method according to claim 11, wherein in the second of the two modes, when a predetermined condition is not detected by the monitor, the control apparatus causes the liquid material to be disposed from the discharge device.

19. The method according to claim 11, wherein the detecting apparatus detects a number or forms of particle bodies as the detected condition of the particle bodies.

20. The discharge device according to claim 1, wherein the control apparatus selects, when the detected condition includes no particle body, the second of the two modes.

21. The discharge device according to claim 1, wherein the control apparatus selects, when the detected condition includes no particle body or two or more particle bodies, the second of the two modes.

22. The discharge device according to claim 1, wherein the monitor includes a first region that is connected to the nozzle opening and a second region that follows the first region, the detection apparatus acquires a condition in the first region of the monitor as a first detected condition and a condition in the second region as a second detected condition, and the control apparatus is operable, when the first detected condition includes zero or two or more particle bodies or when the second detected condition includes one or more particles, to select the second of the two modes.

23. The method according to claim 11, wherein the selectively controlling includes selecting, when the detected condition includes no particle body, the second of the two modes.

24. The method according to claim 11, wherein the selectively controlling includes selecting, when the detected condition includes no particle body or two or more particle bodies, the second of the two modes.

25. The method according to claim 11, wherein the acquiring the detection result includes setting, in the monitor, a first region that is connected to the nozzle opening and a second region that follows the first region, and acquiring a condition of the first region as a first detected condition and a condition of the second region as a second detected, and the controlling includes selecting the second of the two modes, when the first detected condition includes zero or two or more particle bodies or when the second detected condition includes one or more particles.

26. A discharge device comprising a discharge head comprising a cavity, a monitor, and a nozzle opening, wherein the cavity is upstream of the monitor, and the monitor includes the nozzle opening, such that the nozzle opening connected to the cavity via the monitor;

an actuator that deforms a wall of the cavity to fluctuate an internal volume of the cavity and change an internal pressure of the cavity to supply a liquid material to the monitor and cause the liquid material to be discharged;

the discharge device discharges the liquid material as a plurality of individual droplets from the nozzle opening, the monitor configured to hold the liquid material to be discharged as a next one of the plurality of droplets from the nozzle opening;

a detection apparatus that detects a condition of particle bodies included in the liquid material immediately before discharge from the nozzle opening at the monitor, wherein the condition includes a number of the particle bodies in a droplet to be discharged next from the nozzle opening and the detection apparatus is configured to pick-up an image through a light transmissive part of the monitor to detect the condition as a detected condition; and a control apparatus that selectively controls the discharge device in one of two modes depending on the detected condition, when the detected condition is within a predetermined range, the actuator fluctuates the internal pressure, upstream of the monitor, in a range that causes the liquid material to be discharged from the nozzle opening as an individual droplet to a designated target, and in a second of the two modes, when the detected condition is not within the predetermined range, the control apparatus disposes the individual droplet from the discharge device.

27. The discharge device according to claim 26, wherein the monitor includes a first region that is connected to the nozzle opening and a second region that follows the first region, the detection apparatus acquires a condition in the first region of the monitor as a first detected condition and a condition in the second region as a second detected condition, and the control apparatus is operable, when the first detected condition is outside a range of a first predetermined condition or when the second detected condition is outside a range of a second predetermined condition, to select the second of the two modes.

28. The discharge device according to claim 26, further comprising a tubular member that holds the liquid material and part of which is shaped so as to form the cavity whose internal pressure is varied by the actuator attached to an outside of the tubular member, the nozzle opening being provided at one end of the tubular member, wherein the monitor is provided between the cavity and the nozzle opening of the tubular member.

* * * * *